United States Patent [19]
Finn et al.

[11] Patent Number: 6,153,645
[45] Date of Patent: Nov. 28, 2000

[54] HETEROCYCLES AS ANTIMICROBIAL AGENTS

[75] Inventors: John Finn, Andover; Xiang Yang Yu, Billerica; Zhongguo Wang, Malden; Jason Hill, Newton, all of Mass.; Dennis Keith, Montclair, N.J.; Paul Gallant, Dedham; Philip Wendler, Sudbury, both of Mass.

[73] Assignee: Cubist Pharmaceuticals, Inc., Cambridge, Mass.

[21] Appl. No.: 09/393,505

[22] Filed: Sep. 10, 1999

Related U.S. Application Data

[60] Provisional application No. 60/100,809, Sep. 18, 1998, and provisional application No. 60/102,695, Oct. 1, 1998.

[51] Int. Cl.[7] .......................... A61K 31/34; A61K 31/40; C07D 493/04; C07D 491/048
[52] U.S. Cl. .......................... 514/468; 514/287; 514/288; 514/410; 514/453; 514/469; 514/470; 546/64; 546/65; 546/66; 546/113; 546/116; 548/421; 548/453; 549/42; 549/50; 549/298; 549/305
[58] Field of Search ...................................... 514/287, 288, 514/410, 453, 468, 469, 470; 549/42, 50, 299, 305; 546/64, 65, 66, 113, 116; 548/421, 453

[56] References Cited

U.S. PATENT DOCUMENTS

| | | | |
|---|---|---|---|
| 5,686,459 | 11/1997 | Diederich et al. | 514/260 |
| 5,726,195 | 3/1998 | Hill et al. | 514/382 |

FOREIGN PATENT DOCUMENTS

| | | |
|---|---|---|
| 0 290 902 | 5/1988 | European Pat. Off. . |
| 0 728 758 | 2/1996 | European Pat. Off. . |
| 6-306096 | 11/1994 | Japan . |
| WO 94/03458 | 2/1994 | WIPO . |
| WO 97/05132 | 2/1997 | WIPO . |
| WO 98/41215 | 9/1998 | WIPO . |

OTHER PUBLICATIONS

Chow C.S., et al., "A Structural Basis for RNA–Ligand Interactions," *Chem. Rev*, 1977, pp. 1489–1513.

Herman, T, et al., "RNA as a Drug Target: Chemical, Modelling, and Evolutionary Tools," *Current Opinion in Biotechnology*, 1998, 9:66–73.

Pearson, N.D., "RNA as a Drug Target," *Chemistry & Biology*, 1997, 4:409–414.

A.G. Anastassiou, R.P. Cellura: "Thermal Cycloaddition to Oxonin," J. Chem. Soc. D., 1970, pp. 484–485.

Th. Wagner–Jauregg et al., "33. Neuartige Cycloadditionsreaktionen von 2– und 4–Vinylpyridin mit N–Alkyl–Maleinimiden," Helv. Chim. Acta, vol. 56, No. 1, 1973, pp. 440–449 (no translation provided).

Krysin M. Yu et al Zh.Org.Khim 1989, 25(10), p. 2094 X (English Abstract provided).

Krysin M. Yu et al Khim.Geterotsikl.Soedin 1987, 11, p. 1463 X (English Abstract provided).

Tsuge O et al "Simple Generation of Ester–Stabilized Azomethine Ylides from 2–Amino Esters and Carbonyl Compounds, Stereochemistry of Their Cycloadditions," Bull.Chem.Soc.Jpn 1987, 60(11), p. 4067–4078.

Andrist A et al "Ozonolysis of Tetrahydrophthalimides (Cyclohex–4–ene–1,2–dicarboximides): A Sterically Dependent Unsymmetrical Oxidative Cleavage Reaction," J.Chem.Soc.Perkin Trans 1 1978, 9, p. 918–923.

Prein A et al, "Site Selectivity in the Rhodium(II)–Catalyzed Reaction of –Diazoimides, Ligand and Substituent Effects," Tetrahedron 1997, 53(23), p. 7777–7793.

Tsuge O et al, "Stable Configuration of Ester–Stabilized Azomethine Ylides, Stabilization of Anti–Form by 1,5–Dipolar Interaction and of syn–Form by Hydrogen Bonding," Chem Lett 1986, (8), p. 1271–1274.

Fannes C et al, "Cycloaddition of Olefinic Compounds to2H–1,4–Oxazin–2–ones: Synthesis of 2–Oxa–5–Azabi–cyclo[2,2,2]oct–5–en–3–ones," Synthesis 1992, (7), p. 705–709.

Obst U et al, "Design of Novel, Nonpeptidic, Thrombin Inhibitors and Structure of a Thrombin–Inhibitor Complex," Angew.Chem.Int.Ed.Engl 1995, 34(16), p. 1739–1742.

Galley G. et al, "Polyfunctionalized Pyrrolidines by Stereoselective 1,3–Dipolar Cycloaddition of Azomethine Ylides to Chiral Enones," J.Org.Chem. 1995, 60, pp. 5005–5010.

Grigg G et al, "X=Y–ZH Systems as Potential 1,3–Dipoles–5[1]—Intramolecular Cycloadditions of Imines of – Amino Acid Esters," Tetrahedron 1985, 41(17), p. 3547–3558.

Okamura H et al, "A Base Catalyzed Diels–Alder Reaction of 3–Hydroxy–2–Pyrone," Tetrahedron Lett 1995, 36(33), p. 5939–5942.

Grigg G et al, "X=Y–ZH Systems as Potential 1,3–Dipoles, Part 21[1] Activation of the ZH Proton in Imines" Tetrahedron 1989, 45(6), p. 1723–1746.

Padwa A et al, "Studies on the Intramolecular Cycloaddition Reaction of Isomunchnones Derived from N–Alkenyl Substituted Diazoimides," Tetrahedron 1996, 52(9), p. 3247–3260.

Grigg G et al, "Decarboxylation of –Amino Acids by Pyruvic Acid and its Derivatives, Evidence for Azomethine Ylides in In Vitro Analogues of Pyruvoyl Enzymic Processes," Tetrahedron Lett 1989, 30(21), p. 2841–2844.

Okamura H et al, "Asymmetric Base–Catalyzed Diels–Alder Reaction of 3–Hydroxy–2–Pyrone with N–Methylmaleimide," Chem Lett 1996, (3), p. 193–194.

Amornraksa K et al, "X=Y–ZH Systems as Potential 1,3–Dipoles, Part 8, Pyrrolidines and –Pyrrolines (3,7–Diazabicyclo[3,3,0]octenes) from the Reaction of Imines of – Amino Acids and their Esters with Cyclic Dipolarophiles, Mechanism of Racemisation of –Amino Acids and the Esters in the Presence of Aldehydes," J.Chem.Soc.Perkin Trans 1 1987, 10, p. 2285–2296.

(List continued on next page.)

Primary Examiner—Bernard Dentz
Attorney, Agent, or Firm—Wolf, Greenfield & Sacks, P.C.

[57] ABSTRACT

Methods for treating infection and related compositions, compounds of formula I as defined in the application and methods for preparing same, are provided. In general, the compounds inhibit transfer ribonucleic acid (tRNA) synthetase and are useful as antimicrobial agents.

27 Claims, No Drawings

OTHER PUBLICATIONS

Harwood L et al, "Synthesis of Carboxylated Pyrrolidine Derivatives via 1,3–Dipolar Cycloadditions of Homochiral Double–Stabilised E–Azomethine Ylids," Tetrahedron Asymmetry 1995, 6(7), p. 1557–1560.

Ibata T. et al, "Carbonyl Ylide from 3–Chloro–3–p–nitrophenylcarbene and Acetone," Tetrahedron Lett 1986, 27(37), p. 4383.

Huisgen R et al, "Three–Component Reactions of Diazomalonic Ester, Benzaldehyde, and Electrophilic Olefins," J.Am.Chem.Soc 1982, 104, p. 4953–4954.

Miah S. et al, "Ligand Effects in the Rhodium(II) Catalysed Reactions of Diazoamides and Diazoimides," Tetrahedron 1996, 52(7), p. 2489–2514.

March P. et al, "Carbonyl Ylides from Aldehydes and Carbenes," J.Am.Chem.Soc 1982, 104, p. 4952.

HETEROCYCLES AS ANTIMICROBIAL AGENTS

This application claims priority from Provisional Applications 60/100,809 filed Sep. 18, 1998 and 60/102,695 filed Oct. 1, 1998.

FIELD OF THE INVENTION

This invention relates to the field of transfer ribonucleic acid (tRNA) synthetase inhibitors, their preparation and their use as antimicrobial agents.

BACKGROUND OF THE INVENTION

Aminoacyl tRNA synthetases (aaRS) are a family of essential enzymes that are found in virtually every biological cell and are responsible for maintaining the fidelity of protein synthesis. They specifically catalyze the aminoacylation of tRNA in a two step reaction:

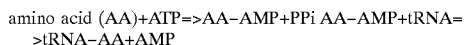

amino acid (AA)+ATP=>AA-AMP+PPi AA-AMP+tRNA=>tRNA-AA+AMP

The enzyme binds adenosine triphosphate (ATP) and its specific amino acid to catalyze formation of an aminoacyl adenylate complex (AA–AMP) with concomitant release of pyrophosphate (PPi). In the second step, the amino acid is transferred to the 2' or 3' terminus of the tRNA yielding "charged" tRNA and adenosine monophosphate (AMP). The charged tRNA delivers the amino acid to the nascent polypeptide chain on the ribosome.

There are at least twenty essential enzymes in this family for each organism. Inhibition of any of the essential tRNA synthetases disrupts protein translation, ultimately resulting in growth inhibition. Pseudomonic acid A, an antibacterial agent currently used in human therapy, provides clear evidence of the utility of tRNA synthetase inhibitors as useful pharmaceuticals. Pseudomonic acid A binds to one particular tRNA synthetase, isoleucyl tRNA synthetase, and inhibits isoleucyl adenylate formation in several Gram positive bacterial pathogens such as *Staphylococcus aureus*, resulting in the inhibition of protein synthesis, followed by growth inhibition.

Novel synthetic compounds which target tRNA synthetases offer clear advantages as useful therapeutic agents to curb the threat of drug resistance. Drug resistance allows a pathogen to circumvent the biochemical disruption caused by an antimicrobial agent. This resistance can be a result of a mutation that has been selected for and maintained. Pathogens in the environment have had repeated exposure to current therapeutics. This exposure has led to the selection of variant antimicrobial strains resistant to these drugs. Novel synthetic antimicrobial agents, therefore, would be expected to be useful to treat drug resistant pathogens, since the pathogen has never been exposed to the novel antimicrobial agent. The development of compounds or combinations of compounds targeting more than one tRNA synthetase is also advantageous. Accordingly, inhibition of more than one enzyme should reduce the incidence of resistance since multiple mutations in a pathogen would be required and are statistically rare.

SUMMARY OF THE INVENTION

The present invention discloses novel compounds which inhibit tRNA synthetases and have efficacy, including whole cell killing, against a broad spectrum of bacteria and fungi. Described herein are compounds which exhibit tRNA synthetase inhibition.

The present invention comprises, in one aspect, compounds of Formula I.

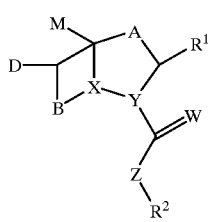

(I)

Each of substituents $R^1$ and $R^2$ of Formula I is independently aryl or heteroaryl.

Group A of Formula I is selected from

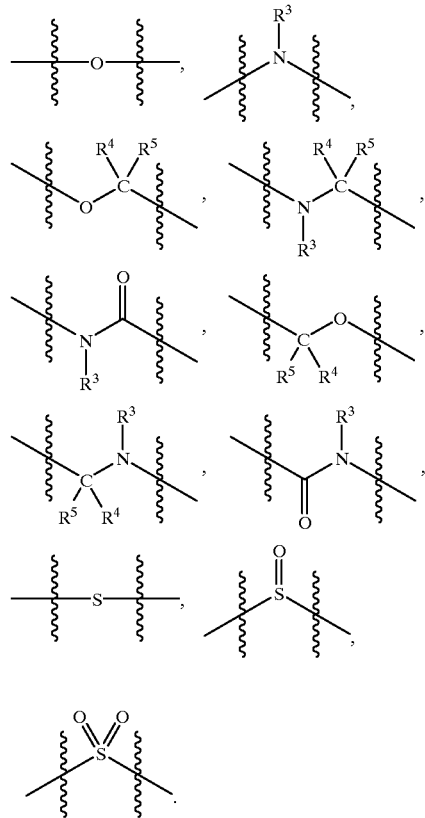

wherein $R^3$ is selected from hydrido, alkyl, carboalkoxy, carboxyamido. Preferred alkyl groups of $R^3$ are unsubstituted alkyl, carboalkoxysubstituted methylene, alkoxy substituted methylene and carboxy substituted methylene.

Each of groups X and Y of Formula I is independently selected from CH or N.

Group Z of Formula I is selected from

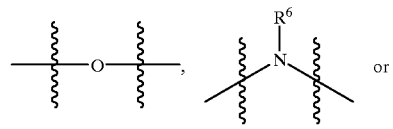 or

-continued

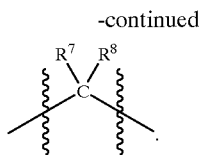

Group M of Formula I is selected from hydrido, alkyl, aryl, carboxy or carboalkoxy.

Group D of Formula I is selected from hydrido, aryl, heteroaryl, or alkyl. Alternatively, group M and group D together are

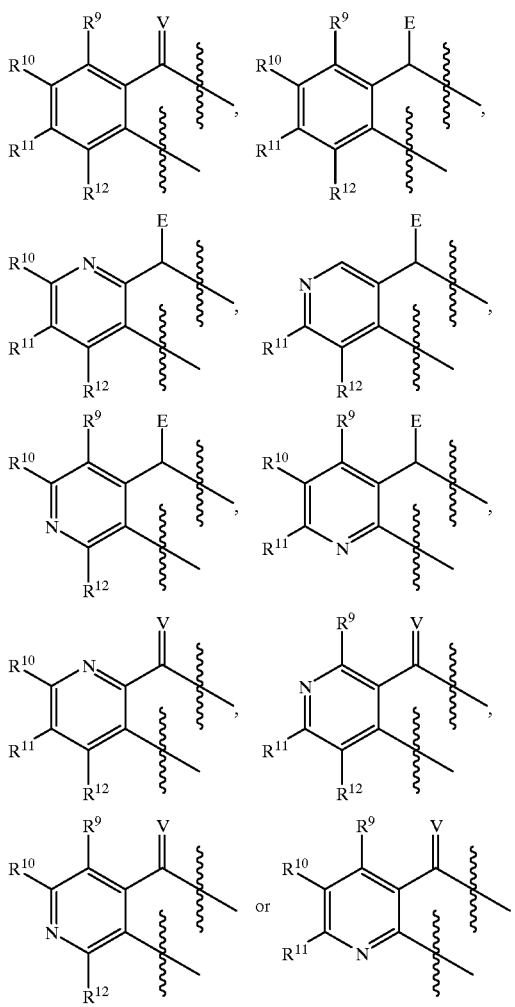

wherein each of $R^9$, $R^{10}$, $R^{11}$, and $R^{12}$ is independently selected from hydrido, halo, alkoxy and alkyl; wherein E is selected from hydrido, hydroxy, alkoxy, aryloxy, halo or amino and wherein V and W are independantly selected from

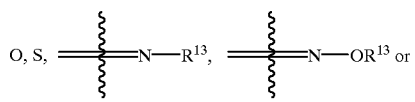

-continued

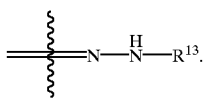

Group B of Formula I is selected from

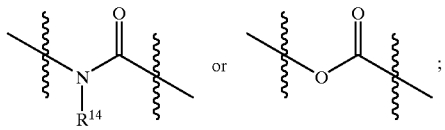

wherein each of $R^4$, $R^5$, $R^6$, $R^7$, $R^8$, $R^{13}$, and $R^{14}$ is independently selected from alkyl and hydrido.

The invention also embraces pharmaceutically-acceptable salts of the forgoing compounds.

A further aspect of the invention comprises using a composition comprising the compound(s) of Formula I to inhibit a tRNA synthetase and in particular, to modulate the growth of bacterial or fungal organisms in mammals, a plant or a cell culture.

Yet another aspect of the invention involves a method of inhibiting the growth of microorganisms. The method involves exposing the microorganism to a compound of the invention, preferably a compound of Formula I, under conditions whereby a therapeutically effective amount of the compound enters the microorganism. The method is useful for inhibiting the growth of microrganisms in vivo and in vitro.

Another aspect of the invention is a pharmaceutical composition comprising the compound(s) of the invention and, in particular, the compounds of Formula I, useful in the treatment of microbial infections, e.g., bacterial infections, fungal infections. A related aspect of the invention is a method of making a medicament which involves placing a compound(s) of the invention, preferably a compound of Formula I, in a suitable pharmaceutically acceptable carrier.

These and other aspects of the invention will be more apparent in reference to the following detailed description of the invention.

DETAILED DESCRIPTION OF THE INVENTION

I. Definitions

Molecular terms, when used in this application, have their common meaning unless otherwise specified. The term "hydrido" denotes a single hydrogen atom (H). The term "acyl" is defined as a carbonyl radical attached to an alkyl, alkenyl, alkynyl, cycloalkyl, heterocycyl, aryl or heteroaryl group, examples of such radicals being acetyl and benzoyl. The term "amino" denotes a nitrogen radical containing two substituents independently selected from the group consisting of hydrido, alkyl, cycloalkyl, heterocyclyl, aryl, and heteroaryl. The term "acyloxy" denotes an oxygen radical adjacent to an acyl group. The term "acylamino" denotes a nitrogen radical adjacent to an acyl group. The term "carboalkoxy" is defined as a carbonyl radical adjacent to an alkoxy or aryloxy group. The term "carboxyamido" denotes a carbonyl radical adjacent to an amino group. The term "carboxy" embraces a carbonyl radical adjacent to an alkyl, alkenyl, alkynyl, cycloalkyl, heterocyclyl, aryl or heteroaryl group. The term "halo" is defined as a bromo, chloro, fluoro or iodo radical. The term "thio" denotes a radical containing a substituent group independently selected from hydrido, alkyl, cycloalkyl, heterocyclyl, aryl and heteroaryl, attached to a divalent sulfur atom, such as, methylthio and phenylthio.

The term "alkyl" is defined as a linear or branched, saturated radical having one to about ten carbon atoms unless otherwise specified. Preferred alkyl radicals are "lower alkyl" radicals having one to about five carbon atoms. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkyl groups include methyl, tert-butyl, isopropyl, and methoxymethyl. The term "alkenyl" embraces linear or branched radicals having two to about twenty carbon atoms, preferably three to about ten carbon atoms, and containing at least one carbon-carbon double bond. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkenyl groups include ethylenyl or phenyl ethylenyl. The term "alkynyl" denotes linear or branched radicals having from two to about ten carbon atoms, and containing at least one carbon-carbon triple bond. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkynyl groups include propynyl. The term "aryl" denotes aromatic radicals in a single or fused carbocyclic ring system, having from five to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of aryl groups include phenyl, naphthyl, biphenyl, terphenyl. "Heteroaryl" embraces aromatic radicals which contain one to four hetero atoms selected from oxygen, nitrogen and sulfur in a single or fused heterocyclic ring system, having from five to fifteen ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of heteroaryl groups include, pyridinyl, thiazolyl, thiadiazoyl, isoquinolinyl, pyrazolyl, oxazolyl, oxadiazoyl, triazolyl, and pyrrolyl groups.

The term "cycloalkyl" is defined as a saturated or partially unsaturated carbocyclic ring in a single or fused carbocyclic ring system having from three to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of a cycloalkyl group include cyclopropyl, cyclobutyl, cyclohexyl, and cycloheptyl. The term "heterocyclyl" embraces a saturated or partially unsaturated ring containing zero to four hetero atoms selected from oxygen, nitrogen and sulfur in a single or fused heterocyclic ring system having from three to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of a heterocyclyl group include morpholinyl, piperidinyl, and pyrrolidinyl. The term "alkoxy" denotes oxy-containing radicals substituted with an alkyl, cycloalkyl or heterocyclyl group. Examples include methoxy, tert-butoxy, benzyloxy and cyclohexyloxy. The term "aryloxy" denotes oxy-containing radicals substituted with an aryl or heteroaryl group. Examples include phenoxy. The term "sulfoxy" is defined as a hexavalent sulfur radical bound to two or three substituents selected from the group consisting of oxo, alkyl, cycloalkyl, heterocyclyl, aryl and heteroaryl, wherein at least one of said substituents is oxo.

The pharmaceutically-acceptable salts of the compounds of the invention (preferably a compound of Formula I) include acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of the invention (preferably a compound of Formula I) may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention (preferably a compound of Formula I) include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine and procaine. All of these salts may be prepared by conventional means from the corresponding compound of the invention (preferably a compound of Formula I) by treating, for example, the compound of the invention (preferably a compound of Formula I) with the appropriate acid or base.

As used herein, "treating" means preventing the onset of, slowing the progression of, or eradicating the existence of the condition being treated, such as a microbial infection. Successful treatment is manifested by a reduction and, preferably, an eradication of the bacterial and/or fungal infection in the subject being treated.

The compounds of the invention (preferably compounds of Formula I) can possess one or more asymmetric carbon atoms and are thus capable of existing in the form of optical isomers as well as in the form of racemic or non-racemic mixtures thereof. The compounds of the invention (preferably compounds of Formula I) can be utilized in the present invention as a single isomer or as a mixture of stereochemical isomeric forms. Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention (preferably compounds of Formula I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention (preferably compounds of Formula I) can likewise be obtained by utilizing optically active starting materials. These isomers may be in the form of a free acid, a free base, an ester or a salt.

The invention also embraces isolated compounds. An isolated compound refers to a compound which represents at least 10%, preferably 20%, more preferably 50% and most preferably 80% of the compound present in the mixture, and exhibits a detectable (i.e. statistically significant) antimicrobial activity when tested in conventional biological assays such as those described herein.

II. Description P According to one aspect of the invention, compounds of Formula I are provided. The compounds are useful for inhibiting the enzymatic activity of a tRNA synthetase in vivo or in vitro. The compounds are particularly useful as antimicrobial agents, i. e., agents which inhibit the growth of bacteria or fungii.

One sub-class of compounds of Formula I are compounds of Formula II

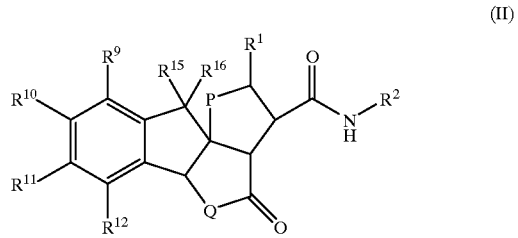

(II)

Each of groups P and Q of Formula II is independently selected from O and NH.

Groups $R^{15}$ and $R^{16}$ together are W. Alternatively, each of $R^{15}$ and $R^{16}$ is independently selected from hydrido, hydroxy, alkoxy, aryloxy and carboalkoxy, with the proviso that when $R^{15}$ and $R^{16}$ together are not W, at least one of $R^{15}$ or $R^{16}$ must be hydrido. Substituents $R^1$, $R^2$, $R^9$, $R^{10}$, $R^{11}$, $R^{12}$, $R^{13}$ and W are as previously described.

The compounds of the invention (preferably compounds of Formula I) are active against a variety of bacterial organisms. They are active against both Gram positive and Gram negative aerobic and anaerobic bacteria, including Staphylococci, for example *S. aureus;* Enterococci, for example *E. faecalis;* Streptococci, for example *S. pneumoniae;* Haemophilus, for example *H. influenza;* Moraxella, for example *M. catarrhalis;* and Escherichia, for example *E. coli.* The compounds of the present invention (preferably compounds of Formula I) are also active against Mycobacteria, for example *M. tuberculosis.* The compounds of the present invention (preferably compounds of Formula I) are also active against intercellular microbes, for example Chlamydia and Rickettsiae. The compounds of the present invention (preferably compounds of Formula I) are also active against Mycoplasma, for example *M. pneumoniae.*

The compounds of the present invention (preferably compounds of Formula I) are also active against fungal organisms, including, among other organisms, the species Aspergillus, Blastomyces, Candida, Coccidioides, Cryptococcus, Epidermophyton, Hendersonula, Histoplasma, Microsporum, Paecilomyces, Paracoccidioides, Pneumocystis, Trichophyton, and Trichosporium.

In a second aspect the invention provides a pharmaceutical composition comprising a compound of the invention, preferably a compound in accordance with the first aspect of the invention, and a pharmaceutically-acceptable carrier (described below). As used herein the phrase "therapeutically-effective amount" means that amount of a compound of the present invention (preferably a compound of Formula I) which prevents the onset of, alleviates the symptoms of, or stops the progression of a microbial infection. The term "microbial" means bacterial and fungal, for example a "microbial infection" means a bacterial or fungal infection. The term "treating" is defined as administering, to a subject, a therapeutically-effective amount of a compound of the invention (preferably a compound of Formula I). The term "subject", as described herein, is defined as a mammal, a plant or a cell culture.

According to another aspect of the invention, a method for inhibiting a tRNA synthetase is provided which comprises contacting a tRNA synthetase with a compound of the invention (preferably a compound of Formula I) under the conditions whereby the tRNA synthetase interacts with its substrates and its substrates react(s) to form an aminoacyl adenylate intermediate and, preferably, react(s) further to form a charged tRNA. Such conditions are known to those skilled in the art (see also e. g., the Examples for conditions), and PCT/US 96/11910, filed Jun. 18, 1996 (WO 97/05132, published Feb. 13, 1997), and U.S. Pat. No. 5,726,195. This method involves contacting a tRNA synthetase with an amount of compound of the invention (preferably a compound of Formula I) that is sufficient to result in detectable tRNA synthetase inhibition. This method can be performed on a tRNA synthetase that is contained within an organism or outside an organism.

In a further aspect, the invention provides a method for inhibiting the growth of microorganisms, preferably bacteria or fungi, comprising contacting said organisms with a compound of the invention (preferably a compound of Formula I) under conditions which permit entry of the compound into said organism and into said microorganism. Such conditions are known to one skilled in the art and are exemplified in the Examples. This method involves contacting a microbial cell with a therapeutically-effective amount of compound(s) of the invention (preferably compound(s) of Formula I), e.g. to inhibit cellular tRNA synthetase in vivo or in vitro. This method is used in vivo, for example, for treating microbial infections in mammals. Alternatively, the method is used in vitro, for example, to eliminate microbial contaminants in a cell culture, or in a plant.

In accordance with another aspect of the invention, the compositions disclosed herein are used for treating a subject afflicted by or susceptible to a microbial infection. The method involves administering to the subject a therapeutically effective amount of a compound of the invention (preferably a compound of Formula I). According to this aspect of the invention, the novel compositions disclosed herein are placed in a pharmaceutically acceptable carrier and are delivered to a recipient subject (preferably a human) in accordance with known methods of drug delivery. Exemplary procedures for delivering an antibacterial, antifungal and antimycoplasmal agent are described in U.S. Pat. No. 5,041,567, issued to Rogers and in PCT patent application No. EP94/02552 (publication no. WO 95/05384), the entire contents of which documents are incorporated in their entirety herein by reference. In general, the methods of the invention for delivering the compositions of the invention in vivo utilize art-recognized protocols for delivering the agent with the only substantial procedural modification being the substitution of the compounds of the invention (preferably compounds of Formula I) for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the invention (preferably compounds of Formula I) for the agents used in the art-recognized protocols.

The pharmaceutical preparations disclosed herein are prepared in accordance with standard procedures and are administered at dosages that are selected to reduce, prevent or eliminate the infection (See, e. g., Remington's Pharmaceutical Sciences, Mack Publishing Company, Easton, Pa. and Goodman and Gilman's The Pharmaceutical Basis of Therapeutics, Pergamon Press, New York, N.Y., the contents of which are incorporated herein by reference, for a general description of the methods for administering various antimicrobial agents for human therapy). The compositions of the invention (preferably of Formula I) can be delivered using controlled ( e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. Nos. 4,452,775 (issued to Kent), 5,239,660 (issued to Leonard), 3,854,480 (issued to Zaffaroni).

The pharmaceutically-acceptable compositions of the present invention comprise one or more compounds of the invention (preferably compounds of Formula I) in association with one or more nontoxic, pharmaceutically-acceptable carriers and/or diluents and/or adjuvants and/or excipients, collectively referred to herein as "carrier" materials, and if desired other active ingredients.

The compounds of the present invention (preferably compounds of Formula I) are administered by any route, preferably in the form of a pharmaceutical composition adapted to such a route, as illustrated below and are dependent on the condition being treated. The compounds and compositions can be, for example, administered orally, intravascularly, intraperitoneally, subcutaneously, intramuscularly or topically.

For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions can be administered via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery.

The dosage regimen for treating an infection with the compound and/or compositions of this invention is selected in accordance with a variety of factors, including the type, age, weight, sex and medical condition of the patient, the severity of the infection, the route and frequency of administration and the particular compound employed. In general, dosages are determined in accordance with standard practice for optimizing the correct dosage for treating an infection.

The compositions can contain from 0.1% to 99% by weight, preferably 10–60% by weight, of the active ingredient, depending on the method of administration. If the compositions contain dosage units, each dosage unit preferably contains from 50–500 mg of the active material. For adult human treatment, the dosage employed preferably ranges from 100 mg to 3 g, per day, depending on the route and frequency of administration.

If administered as part of a total dietary intake, the amount of compound employed can be less than 1% by weight of the diet and preferably no more than 0.5% by weight. The diet for animals can be normal foodstuffs to which the compound can be added or it can be added to a premix.

Further references to features and aspects of the invention are provided in the Examples set out hereafter.

EXAMPLES

The following Examples are detailed descriptions of the methods of preparation of compounds of Formula I. These detailed preparations fall within the scope of, and serve to exemplify, the invention. These Examples are presented for illustrative purposes only and are not intended as a limitation on the scope of the invention.

GENERAL SYNTHETIC PROCEDURES

General Procedure 1

Reaction 1

Compound 1 can be converted to compound 2 by treatment with F in the presence of a base such as piperidine or potassium hydroxide or an acid such as acetic acid in an appropriate solvent such as ethanol, tetrahydrofuran, methanol or acetic anhydride at temperatures ranging from ambient to the boiling point of the solvent.

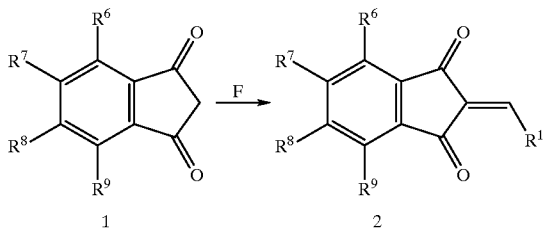

wherein $R^1$ and $R^6$–$R^9$ are as previously defined and F is an aldehyde or its synthetic equivalent an imine or acetal such as benzaldehyde, 3-pyridine carboxaldehyde or benzaldehyde dimethylacetal. (for analogous procedures see Franz, C. et al Heterocycles; 1995, 41(11), 2527. Krasnaya, ZH. A. et al Izv Akad Nauk SSSR, Ser khim 1990, 11, 2561. Hennig, L. et al Montsh Chem 1992, 123, 571.

Reaction 2

Compound 2 can be converted to compound 3 by treatment with H in an appropriate solvent such as methanol or water at temperatures ranging from 0 C. to ambient.

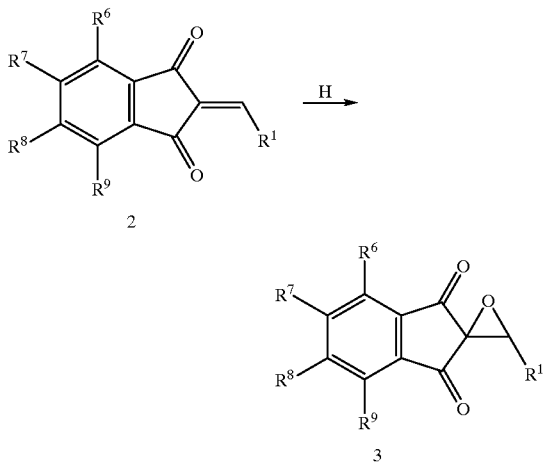

wherein $R^1$ and $R^6$–$R^9$ are as previously defined and H is a reagent capable of transferring an oxygen atom to a double bond such as hydrogen peroxide or dimethyl dioxirane.

Reaction 3

Compound 3 can be converted to compound 5 by treatment with compound 4 in an appropriate solvent such as benzene, carbon tetrachloride or toluene at temperatures ranging from 50 C. to the boiling point of the solvent.

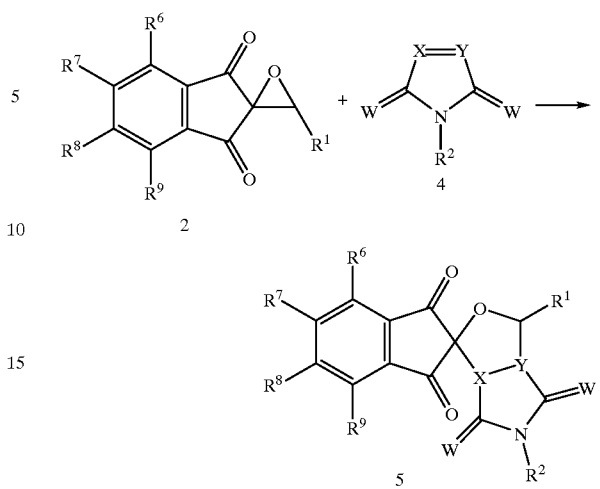

Wherein $R^1$, $R^2$, $R^6$–$R^9$, W, X and Y are as previously defined, (for analogous procedures see Krysin, M. Yu. et al Khim. Geterotsikl. Soedin 1987, 11, 1463)

Reaction 4

Compound 5 can be converted to compound 6 by treatment with I in an appropriate solvent such as methanol, ethanol or tetrahydrofuran at temperatures ranging from 0 C. to ambient.

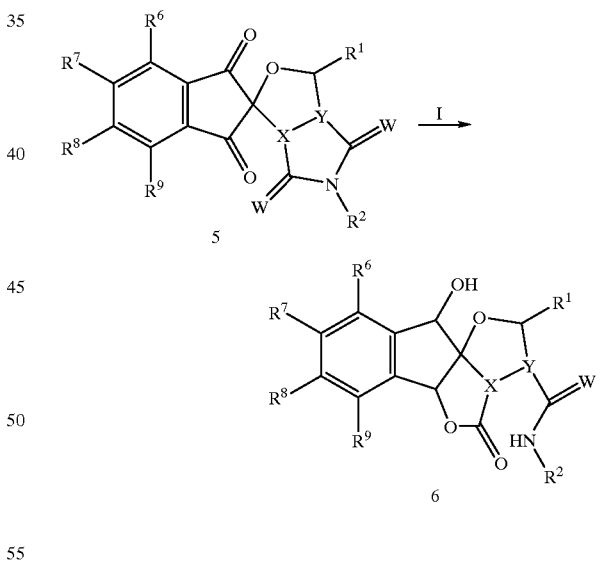

Wherein $R^1$, $R^2$, $R^6$–$R^9$, W, X and Y are as previously defined, wherein I is a reducing agent such as sodium borohydride, sodium hydride, lithium borohydride or sodium triacetoxyborohydride.

Reaction 5

Compound 6 can be converted to compound 7 by treatment with J in an appropriate solvent such as dichloromethane or tetrahydrofuran at temperatures ranging from 0 C. to the boiling point of the solvent.

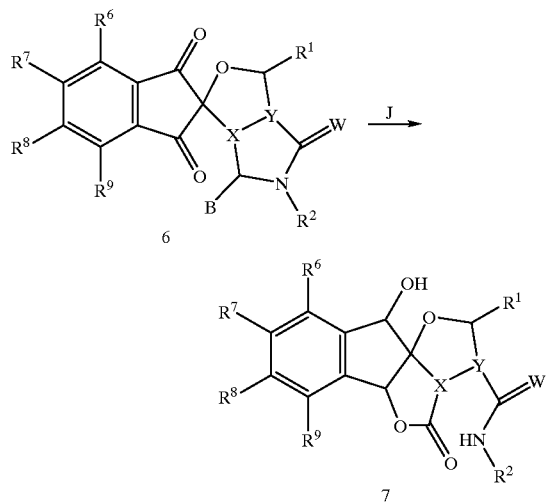

6

7

Wherein $R^1$, $R^2$, $R^6$–$R^9$, W, X and Y are as previously defined, wherein J is an oxidizing agent such as pyridinium chlorochromate or Dess Martin reagent.

General procedure 2

Reaction 1

Compound 3 can be converted to compound 8 by treatment with K in an appropriate solvent such as benzene, carbon tetrachloride or dichloromethane at temperatures ranging from ambient to the boiling point of the solvent.

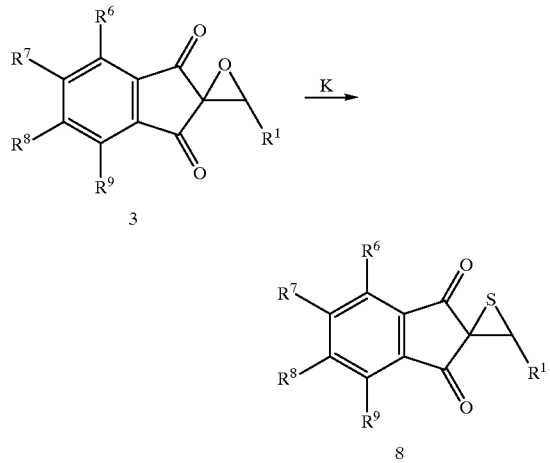

3

8

Wherein $R^1$ and $R^6$–$R^9$ are as previously defined and K is a reagent capable of transferring a sulfur atom to an epoxide such as triphenylphosphinsulfide or potassium thiocyanide. (for analogous procedures see Childers, W. E. et al J. Org. Chem 1988, 53, 5947)

Reaction 2

Compound 8 can be converted to compound 9 by treatment with compound 4 according to reaction 3 of general procedure 1

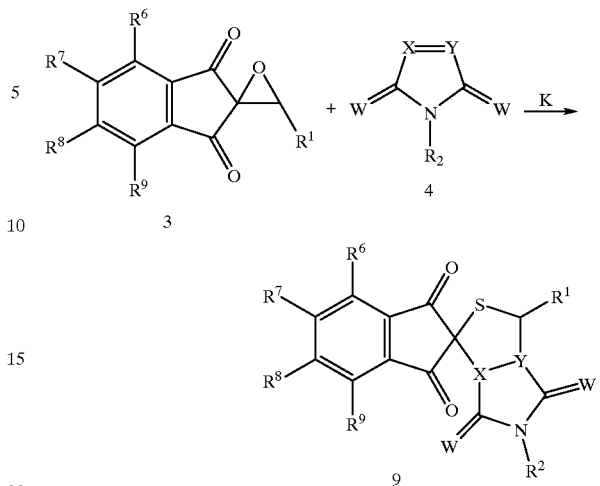

3

4

9

Wherein $R^1$, $R^2$, $R^6$–$R^9$, W, X and Y are as previously defined.

Reaction 3

Compound 9 can be converted to compound 10 by treatment with L in an appropriate solvent such as benzene, carbon tetrachloride or dichloromethane at temperatures ranging from ambient to the boiling point of the solvent.

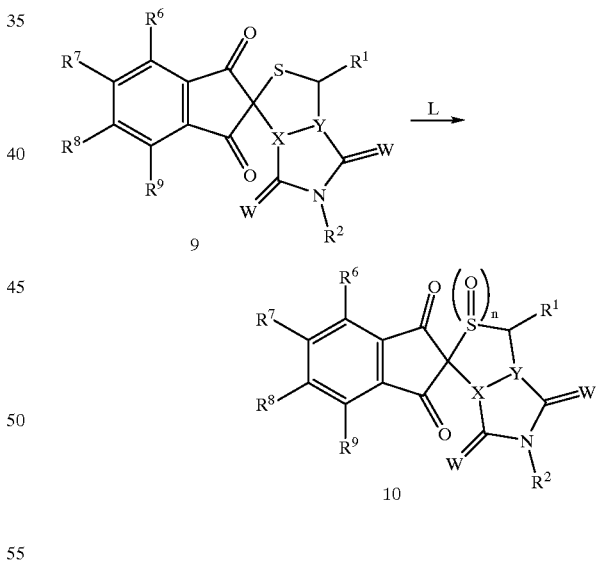

9

10

Wherein $R^1$, $R^2$, $R^6$–$R^9$, W, X and Y are as previously defined, wherein L is an oxidizing such as hydrogen peroxide, 3-chloroperbenzoic acid or sodium metaperiodate, wherein n=1 or2.

Reaction 4

Compound 10 can be converted to compound 11 by treatment with I according to reaction 4 of general procedure 1.

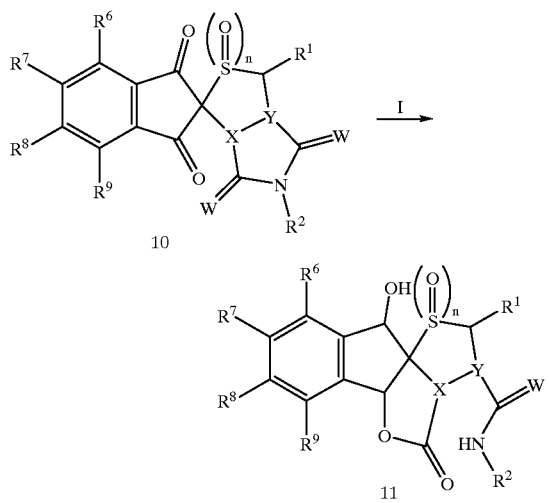

Wherein $R^1$, $R^2$, $R^6$–$R^9$, I, W, X, n and Y are as previously defined.

Reaction 5

Compound 11 can be converted to compound 12 by treatment with J according to reaction 5 of general procedure 1.

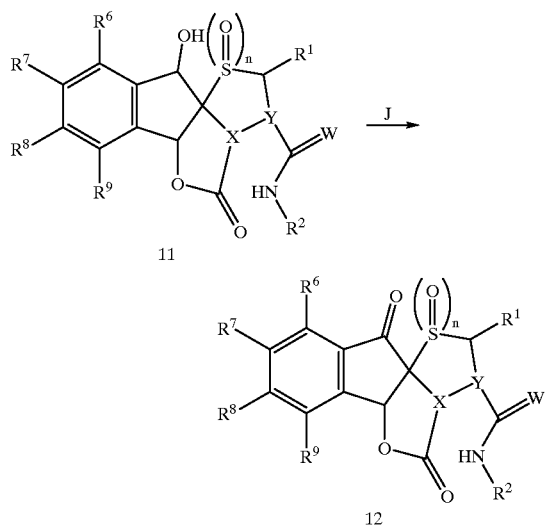

Wherein $R^1$, $R^2$, $R^6$–$R^9$, J, n, W, X and Y are as previously defined.

General procedure 3

Reaction 1

Amino acid 13 can be converted to compound 14 by treatment with compound 4 and N in an appropriate solvent such as benzene, carbon tetrachloride or acetonitrile at temperatures ranging from 50 C. to the boiling point of the solvent.

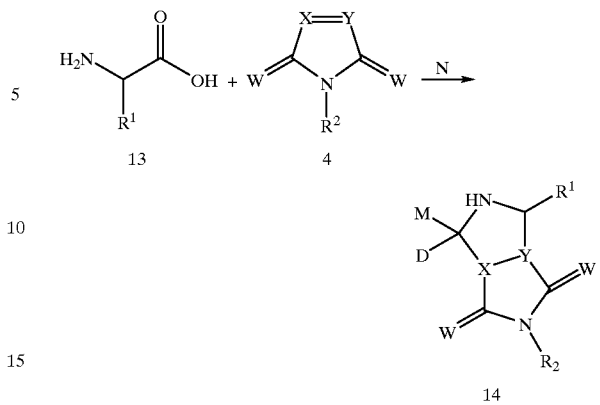

Wherein $R^1$, $R^2$, D, X, Y, W and M are as previously defined, wherein N is an aldehyde or ketone such as benzaldehyde, 2-indanone or 3-pyridine carboxaldehyde.

Reaction 2

Compound 14 can be converted to compound 15 by treatment with O in an appropriate solvent such as benzene, carbon tetrachloride, tetrahydrofuran or acetonitrile at temperatures ranging from 0 C. to the boiling point of the solvent.

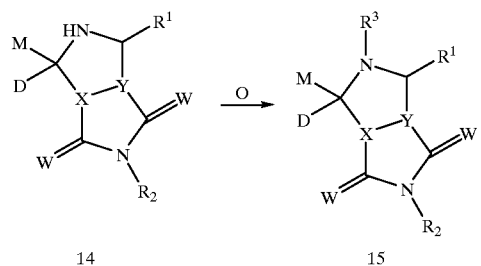

wherein $R^1$, $R^2$, $R^3$, D, X, Y, W and M are as previously defined, wherein O is an isocyanate, chloroformate, acylating or alkylating reagent such as acetyl chloride, methyl iodide phenyl isocyanate or benzylchloroformate.

General procedure 4

Reaction 1

Amine 16 can be converted to compound 17 by treatment with compound 4, R and if appropriate a base such as N-methyl morpholine or diazabicycloundecene in an appropriate solvent such as benzene, tetrahydrofuran or acetonitrile at temperatures ranging from 50 C. to the boiling point of the solvent.

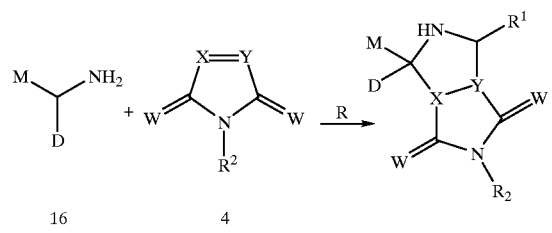

Wherein $R^1$, $R^2$, X, Y and W are as previously defined, wherein at least one of D or M is selected from is a group capable of stabilizing a negative charge such as acyl, aryl, heteroaryl, or carboxy, wherein R is an aldehyde, (for analogous procedures see Grigg, R. et al Tetrahedron 1989, 45(6), 1723. Patzel, M. et al J. Org. Chem. 1995, 60, 5005.)

Reaction 2

Compound 17 can be converted to compound 18 by treatment with O according to reaction 2 of general procedure 3

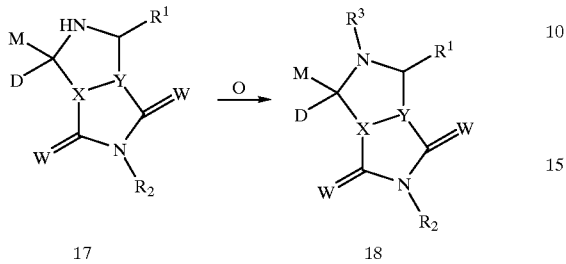

wherein $R^1$, $R^2$, $R^3$, O, X, Y and W are as previously defined, wherein at least one of D or M is selected from a group capable of stabilizing a negative charge such as acyl, aryl, heteroaryl, or carboxy.

General procedure 5

Compound 19 can be converted to compound 20 by treatment with compound 4, N and S at temperatures ranging from 80 C. to 125 C.

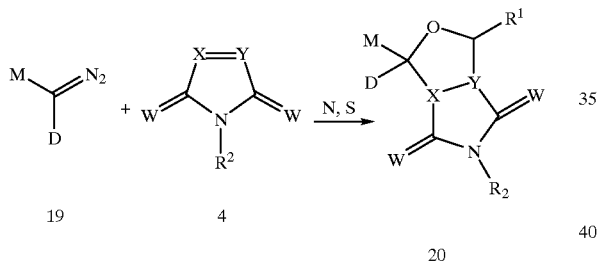

Wherein $R^1$, $R^2$, X, Y and W are as previously defined, wherein at least one of D or M is selected from a group capable of stabilizing a diazo group such as acyl, aryl, heteroaryl, or carboxy, wherein S is a copper salt such as copper triflate or copper acetate, (for analogous procedures see Huisgen, R. et al J. Am.Chem.Soc. 1982, 104, 4953.)

General procedure 6

Reaction 1

Compound 21 can be is converted to compound 22 by treatment with compound 4 in an appropriate solvent such as benzene, toluene or dioxane at temperatures ranging from 80 C. to the boiling point of the solvent.

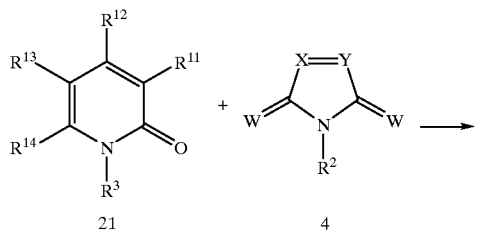

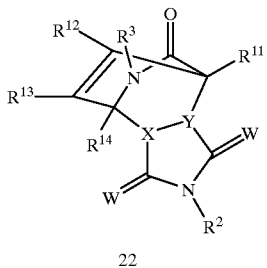

wherein $R^2$, $R^3$, X, Y and W are as previously defined, wherein $R^{11}$–$R^{14}$ are independantly selected from hydrido, alkyl, aryl or heteroaryl. (for analogous procedures see Nakano, H. T. et al Heterocycles 1994, 39(2), 723, ibid 1992, 33(1),195; J. Chem. Soc. Chem. Comm.1990,24,1775)

Reaction 2

Compound 22 can be converted to compound 23 by treatment with T in an appropriate solvent such as methanol, tetrahydrofuran or dioxane at temperatures ranging from 0 C. to the boiling point of the solvent.

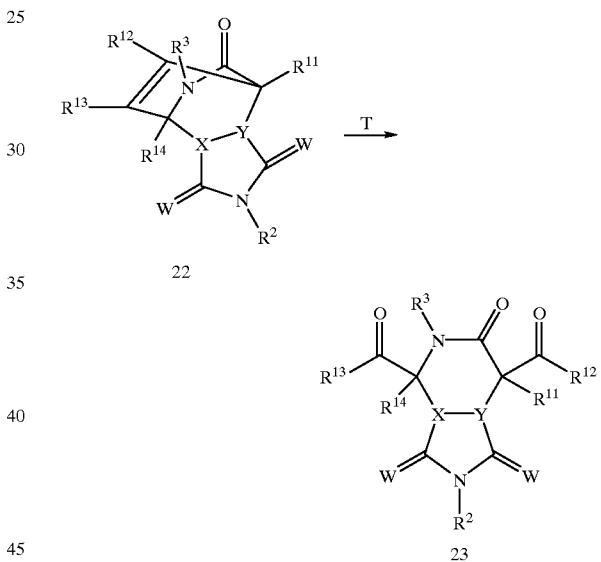

Wherein $R^2$, $R^3$, $R^{11}$–$R^{14}$, X, Y and W are as previously defined, wherein T is a reagent capable of cleaving a double bond such as ozone or sodium periodate/osmium tetroxide.

General procedure 7

Reaction 1

Compound 24 can be converted to compound 25 by treatment with compound 4 according to reaction 1 of General procedure 6.

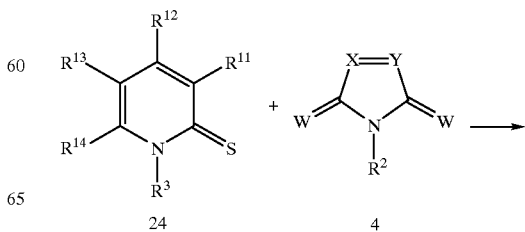

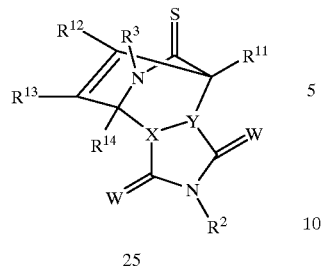

25

Wherein $R^2$, $R^3$, $R^{11}$–$R^{14}$, X, Y and W are as previously defined.

Reaction 2

Compound 25 can be converted to compound 26 by treatment with T according to reaction 2 of General procedure 6.

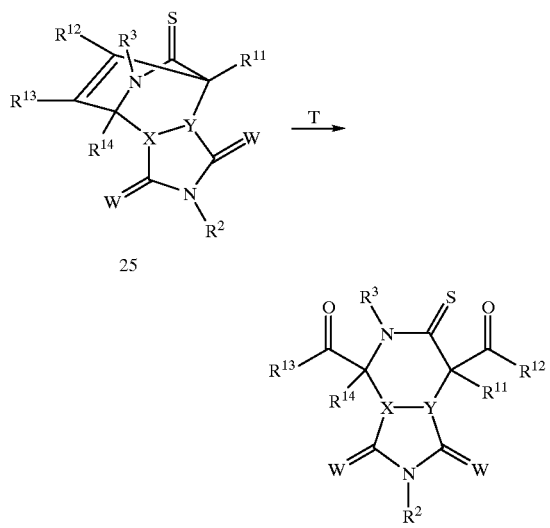

Wherein $R^2$, $R^3$, $R^{11}$–$R^{14}$, T, X, Y and W are as previously defined.

Reaction 3

Compound 26 can be converted to compound 27 by treatment with U in an appropriate solvent such as methanol, ethanol or tetrahydrofuran at temperatures ranging from 0 C. to the boiling point of the solvent.

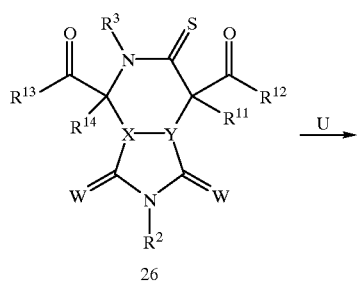

26

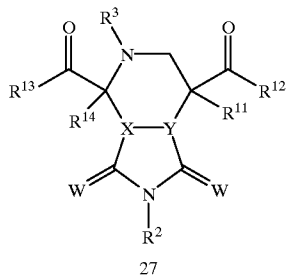

27

Wherein $R^2$, $R^3$, $R^{11}$–$R^{14}$, X, Y and W are as previously defined, wherein U is a reagent capable of reducing a thioanide such Raney nickel or sodium borohydride/nickel (II) chlroride. (for analogous procedures see Milewska, M. J. et al Synthesis 1996, 12,1485. Martin-Martinez, M. et al Tetrahedron 1996, 52(44), 13991.)

General procedure 8

Reaction 1

Compound 28 can be converted to compound 29 by treatment with compound 4 according to reaction 1 of General procedure 6.

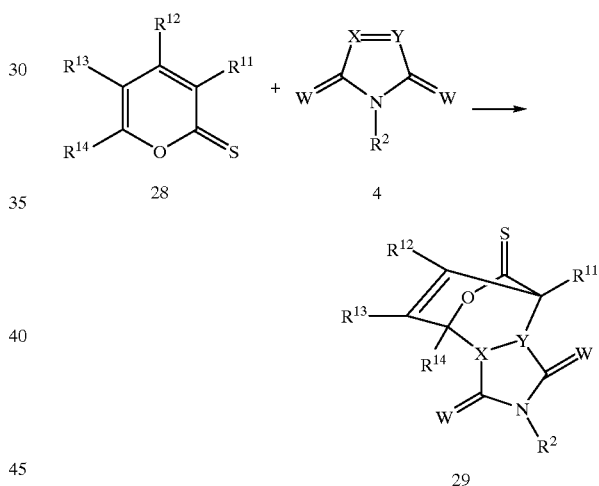

Wherein $R^2$, $R^{11}$–$R^{14}$, X, Y and W are as previously defined. (for analogous procedures see Okamura, H. et al Tetrahedron Lett. 1995, 36(33), 5939, Chem. Lett. 1996, 3, 193.)

Reaction 2

Compound 29 can be converted to compound 30 by treatment with T according to reaction 2 of General procedure 6

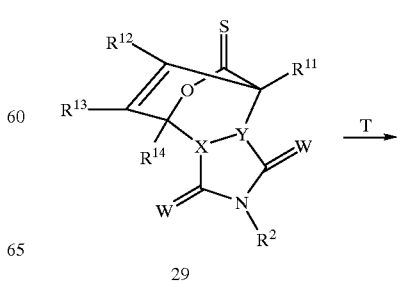

29

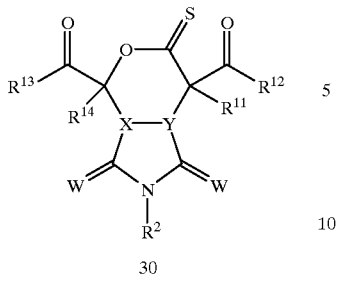

Wherein $R^2$, $R^{11}$–$R^{14}$, T, X, Y and W are as previously defined.

Reaction 3

Compound 30 can be converted to compound 31 by treatment with U according to reaction 3 of General procedure 7

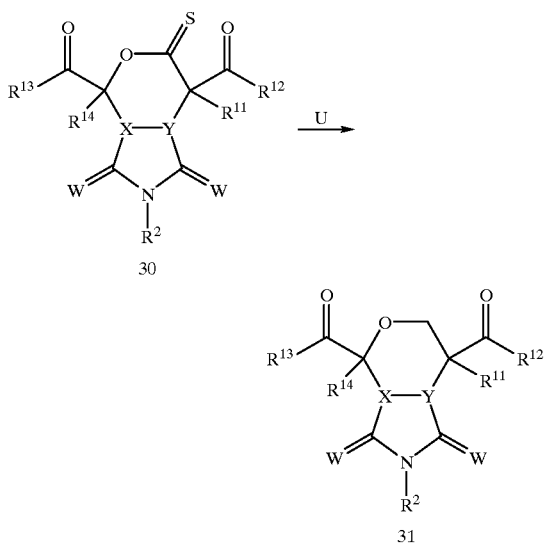

Wherein $R^2$, $R^{11}$–$R^{14}$, U, X, Y and W are as previously defined. (For analogous procedures see Bradshaw, J. S. et al J. Org. Chem. 1983, 48, 1127.)

Compounds 14, 15, 17, 18, 20, 23, 26 and 31 can subsequently be converted to compounds of formula I according to reaction 4 and 5 of general procedure 1 and /or by standard procedures known to those skilled in the art.

Compounds 1, 4, 13, 16, 19, 21, 24 and 28 can be obtained commercially or synthesized by standard procedures known to those skilled in the art. (see Hu, Z. et al J. Org. Chem. 1992, 57(14), 3988; Nishio, T. et al J. Chem. Soc. Perkin Trans. I 1992, 7, 899; Mazurkiewicz, R. et al Pol. J. Chem. 1988, 62(1–3), 115; Becker, Y. et al J. Org. Chem. 1976, 41(14), 2496; Cava, M. P. et al Org. Synth. 1961, 41,93; Pan, H-L. J. Med. Chem. 1970, 13, 565; Yogo, M. et al J. Chem. Soc. Chem. Comm. 1984, 6, 332; Wasserman, H. H. et al Tetrahedron Lett. 1995, 36, 7735; Tatsugi, J. et al Synth. Comm. 1998, 28(5), 859.)

Additional compounds of formula I can be synthesized by substitution of starting materials in general procedures 1–8 with appropriate starting materials known to those skilled in the art.

Method 1 Preparation of examples 1a and 1b

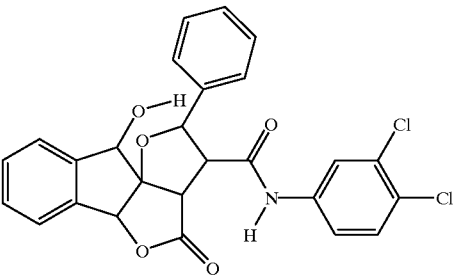

To a solution of maleic anhydride (32 g) in dry diethyl ether (400 ml) was added dichloroaniline (53 g) in dry diethyl ether (30 ml) and the suspension was stirred at room temperature. After 2 hours, the solid was filtered and washed with diethyl ether (3×50 ml). To a suspension of sodium acetate (11 g) in acetic anhydride (110 ml) was added the solid obtained above. The resulting suspension was heated in hot water (75–85 ° C.). After 2 hours the mixture was cooled to room temperature. The precipitate was filtered, washed with ice water (3×100 ml) and dried under reduced pressure at 50° C. for 24 hours to give N-(3,4-dichlorophenyl) maleimide as a yellow solid (64 g).

To a solution of 1,3-indandione (43.8 g) and piperidine (44 mg) in dry benzene (500 ml) was added benzaldhyde (31.8 g). The mixture was heated to reflux and the water generated was removed by Dean-Stark trap. After 24 hours, the mixture was evaporated to dryness. The residue was recrystallized from ethanol (200 ml) to give 2-benzylidene-1,3-indandione as a yellow solid (50.6 g).

To a suspension of 2-benzylidene-1,3-indandione (20 g) in methanol (200 ml) was added 30% hydrogen peroxide (19 ml). The suspension was cooled to 5° C. and 1 N sodium hydroxide (2.1 ml) was added dropwise at such a rate as to keep the temperature below 15 ° C. After completed addition, stirring was continued at room temperature for 30 minutes. The mixture was then poured into water (1.2 L). The resulting crystalline precipitate was collected by filtration, washed on the filter with water (3×100 ml) and dried under high vacuum at room temperature for 24 hours, affording 3-phenylspiro[oxirane-2,2'-indan]-1',3'-dione as a yellow solid (17 g).

3-Phenylspiro[oxirane-2,2'-indan]-1',3'-dione (10 g) and N-(3,4-dichlorophenyl)maleimide (9.7 g) in dry benzene (200 ml) were heated to reflux for 24 hours. The mixture was evaporated to dryness. The residue was purified by silica gel chromatography (20% hexane in dichloromethane). Elution of the column gave the faster moving trans spiro product (4.3 g)

To a solution of sodium borohydride (46 mg) in methanol (100 ml) was added trans spiro compound (600 mg) in THF (20 ml). The mixture was stirred at room temperature for 24 hours and then water (2 ml) was added. The mixture was evaporated to dryness. The residue was dissolved in ethyl acetate (100 ml) and the solution was washed with water (500 ml) and saturated sodium chloride (50 ml). The organic layer was dried over anhydrous sodium sulfate, filtered and evaporated to dryness. The residue was purified by silica gel chromatography (15% ethyl acetate in dichloromethane). Elution of the column gave the faster moving isomer example 1a (210 mg) as a white solid and the slower moving isomer example 1b as a white solid (120 mg).

Method 2 Preparation of example 2

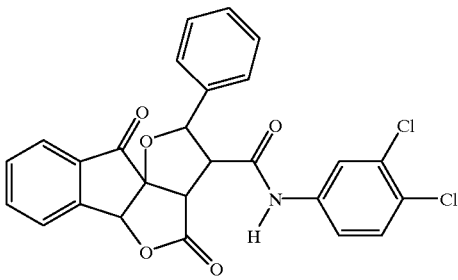

To a solution of examples 1a and 1b (40 mg) in dry acetonitrile (5 ml) was added Dess-Martin reagent (37.6 mg). The mixture was stirred at room temperature for 24 hours. The mixture was evaporated to dryness. The residue was purified by silica gel chromatography (5% ethyl acetate in hexane) to give example 2 (23 mg) as a white solid.

Method 3 Preparation of examples 3a,3b and 3c

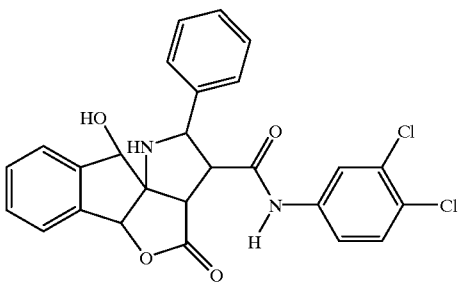

To a stirred solution of (S)-(+)-phenyl glycine (1.204g) in dry acetonitrile (50 mL) was added ninhydrin (1.424g), and 3,4-dichlorophenyl malemide (1.92g) under a nitrogen atmosphere. The resulting solution was heated to reflux for 16 hours, then allowed to cool to room temperature., Evaporation of the solvent gave a yellow solid which was purified by Florisil® (–200 mesh Aldrich Chemical Company, Milwaukee, Wis.) chromatography(5%–30% ethyl acetatelhexanes) to yield the nitrogen spiro compound as a mixture of isomers.

To a stirred solution of nitrogen spiro isomers above (137 mg) in 10 ml of dry methyl alcohol at 0° C. was added 11 mg of sodium borohydride. The solution was warmed to room temperature then stirred for 2 hours. Saturated ammonium chloride (30 mL) and ethyl acetate (40 ml) were added. The layers were separated and the organic phase was washed with saturated sodium chloride then dried over anhydrous sodium sulfate. Evaporation of the solvent gave a white solid. Preparative thin layer chromatography (50% ethyl acetate/10% methylene chloride/40% hexane) yielded a less polar isomer example 3 c (35 mg), a mixture of isomers example 3a (10 mg), and a more polar isomer example 3b (15 mg).

Method 4 Preparation of example 5

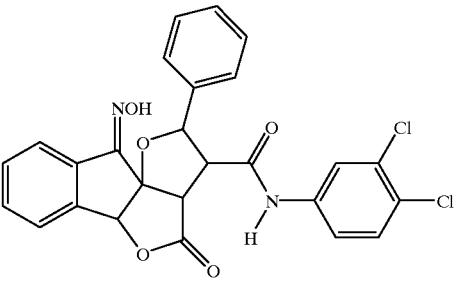

To a solution of example 2 (5 mg) in ethanol (5 ml) was added pyridine (0.1 ml) and hydroxylamine hydrochloride (1 mg). The mixture was stirred at room temperature for 16 hours before the solvent was removed by evaporation. The residue was dissolved in ethyl acetate (25 ml) and washed with water (25 ml), dried over anhydrous magnesium sulfate and evaporated to dryness. The residue was purified by preparative thin layer chromatography eluting with dichloromethane to give example 5 as a solid (3 mg)

Also prepared by method 1 were examples 4a–c by substituting N-(3,4-dichlorophenyl)maleimide with N-(3-chloro-4-methylphenyl)maleimide and reducing both the trans isomer to example 4a and 4b and the cis isomer to compound 4c.

BIOLOGICAL EVALUATION

Enzymatic activity $IC_{50}$ determinations for the aminoacyl-tRNA synthetases (aaRS) isolated from pathogen or HeLa cells were carried out using a modification of the aaRS charging and trichloroacetic acid precipitation assay described previously (see examples: D. Kern et. al., Biochemie, 61, 1257–1272 (1979) and J. Gilbart et. al. Antimicrobial Agents and Chemotherapy, 37(1), 32–38 (1993)). The aaRS enzymes were prepared via standard cloning and expression methods and partially purified or partially purified from pathogen and HeLa cell extracts. The activity of each aaRS enzyme was standardized as trichloroacetic acid precipitable counts (cpm) obtained at 10 minutes reaction time at $K_m$ concentrations of substrates. For practical purposes, the minimal acceptable value is approximately 2000 cpm per 10 minute reaction.

Preincubations for $IC_{50}$ determinations were initiated by incubating partially purified aaRS extracts in 50 mM HEPES (pH 7.5), 0.1 mM EDTA, 0.05 mg/ml bovine serum albumin, 10 mM dithiothreitol and 2.5% dimethyl sulfoxide with and without test compound (e.g. compound of the invention (preferably a compound of Formula I)) in a final volume of 20 microliters in a microtiter plate for 20 minutes at 25 C. Test compounds were typically present as serial dilutions in concentration ranges of 0.35 nM to 35 $\mu$M. Test compound solutions were prepared by dissolving test compound in 100% dimethyl sulfoxide and diluting to the final concentration with 50 mM HEPES, pH 7.5. $IC_{50}$ determinations were typically performed in duplicate with each experiment containing 4–8 concentrations of inhibitor along with two no inhibitor controls.

$IC_{50}$ incubations were initiated by supplementing the preincubation mixture to a final assay concentration of 10 mM $MgCl_2$, 30 mM KCl, 10 mM KF, 50 mM HEPES (pH 7.5), 20 $\mu$M-500 mM ATP, 2–20 $\mu$M [$^3$H] amino acid, and 90–180 $\mu$M crude tRNA in a final volume of 35 microliters.

The reaction was incubated at 25° C. for 5–20 minutes. At specified time points a 15 microliter aliquot was removed and added to a well of a Millipore filtration plate (Multiscreen-FB, MAFB NOB 10) containing 100 microliters of cold 5% (wt/vol) trichloroacetic acid. Trichloroacetic acid precipitable material was collected by filtration on Millipore Multiscreen filtration station, washed twice with cold 5% trichloroacetic acid, twice with water, and dried. Plates were typically allowed to air dry for several hours or they were baked at 50° C. in a vacuum oven for 30 minutes. The radioactivity on the dried plates was quantitated by the addition of Packard Microscint-20 to the wells and counting with a Packard TopCount scintillation counter.

Inhibitor activity was typically reported as a percentage of the control aaRS activity. The $IC_{50}$ value was determined by plotting per cent activity versus compound concentration in the assay and identifying the concentration at which 50% of the activity was remaining.

The $IC_{50}$ values (in $\mu M$) of representative examples of the present invention are listed below. Stereoisomers are tested separately and referred to by the suffix a–d.

| Example # | IC50 E.faecalis PheRS ($\mu M$) |
|---|---|
| 1a | 0.17 |
| 1b | 0.47 |
| 2 | 3.08 |
| 3a | 0.46 |
| 3b | 4.3 |
| 3c | 0.4 |
| 4a | 1.48 |
| 4b | 8.23 |
| 4c | 33.19 |

Whole cell antimicrobial screens

Compounds were tested for antimicrobial activity against a panel of organisms according to standard procedures described by the National Committee for Clinical Laboratory Standards (NCCLS document M7-A3, Vol. 13, No. 25, 1993/NCCLS document M27-P, Vol. 12, No. 25, 1992). Compounds were dissolved in 100% DMSO and were diluted to the final reaction concentration (0.1 $\mu$g/ml–500 $\mu$g/ml) in microbial growth media. In all cases the final concentration of DMSO incubated with cells is less than or equal to 1%. For minimum inhibitory concentration (MIC) calculations, 2-fold dilutions of compounds were added to wells of a microtiter plate containing $5 \times 10^4$ bacteria or fungal cells in a final volume of 200 lambda of an appropriate media (Mueller-Hinton Broth; Haemophilus Test Media; Mueller-Hinton Broth+5% Sheep Blood; or RPMI 1690). Plates were incubated overnight at an appropriate temperature (30° C.–37° C.) and optical densities (measure of cell growth) were measured using a commercial plate reader. The MIC value is defined as the lowest compound concentration inhibiting growth of the test organism. The MIC values (in $\mu$g/ml) of representative examples of the present invention are listed below.

| Example # | MIC S.aureus ($\mu$g/ml) |
|---|---|
| 1a | 3.1 |
| 1b | 6.25 |
| 2 | >100 |
| 3a | 25 |
| 3b | 25 |
| 3c | 12.5 |
| 4a | >100 |
| 4b | >100 |
| 4c | 25 |
| 5 | <100 |

In Vivo Efficacy

Mouse Protection Test

The mouse protection test is an industry standard for measuring the efficacy of a test compound in vivo [for examples of this model see J. J. Clement, et al., *Antimicrobial Agents and Chemotherapy*, 38 (5), 1071–1078, (1994)]. As exemplified below, this test is used to show the in vivo efficacy of the compounds of the present invention against bacteria or fungi.

The in vivo antimicrobial activity of a compound of the invention (preferably a compound of Formula I) hereinafter referred to as test compound, is established by infecting male or female mice (5 mice/dose group×5 doses/compound) weighing 20–25 g intraperitoneally with pathogen inoculum. The inoculum is prepared from a sample of pathogen obtained from the ATCC (for example, ATCC 29213, *S. aureus*; ATCC 14154, *S.aureus*; ATCC 8668, *Strep. pyogenes*; ATCC 25922, *E. coli*; ATCC 29212, *E. faecalis*; ATCC 25238, *M catarrhalis*; and ATCC 90028, *C. albicans*). Each bacterial strain is grown in its appropriate medium at 37° C. for 18 hr, most strains yielding between $10^8$ and $10^9$ colony forming units (CFU)/ml under these conditions. The overnight culture is serially diluted to an appropriate content and then 0.5 ml of each dilution is added to 4.5 ml of 5% hog gastric mucin to prepare the infecting inoculum. Each mouse is injected with 0.5 ml of the inoculum intraperitoneally (i.p.), five animals per dilution. The 50% lethal dose ($LD_{50}$) and the minimal lethal dose (MLD, the dose causing 100% death of the animals) is calculated on the basis of the number of mice surviving after 7 days. The MLD established for each of the pathogens is used as inoculum dose in the mouse protection tests.

The test compound is dissolved in a sterile vehicle appropriate for its method of delivery (for example, 30% HPB (hydroxypropyl-β-cyclodextrin), pH, 7.4 or 0.05M Tris.HCl). A vehicle group (dose=0) serves as a placebo control for each compound and each pathogen. The dose for the test compound is determined based on the MIC data. A series of dilutions of a test compound is prepared in the vehicle. A group of 5 mice are used for each test compound dose and the vehicle. There are 5–6 doses for each compound. Each animal is used for one experiment only.

Mice are infected i.p. with 0.5 ml of the MLD of pathogen in 5% hog gastric mucin by one researcher and immediately administered compound (s.c., p.o. or i.v. in volumes indicated above) by a second researcher. The 50% protective dose ($PD_{50}$) is calculated from the dose-response curve established on the basis of the numbers of mice surviving for 7 days after treatment In each experiment, a group of positive control with a commercially available antibiotic for example, is also included.

All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:

1. A compound of the Formula:

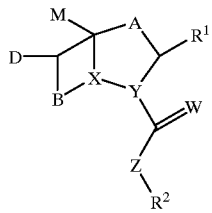

(a) wherein each of $R^1$ and $R^2$ is independently selected from the group consisting of aryl and heteroaryl;
(b) wherein A is selected from the group consisting of

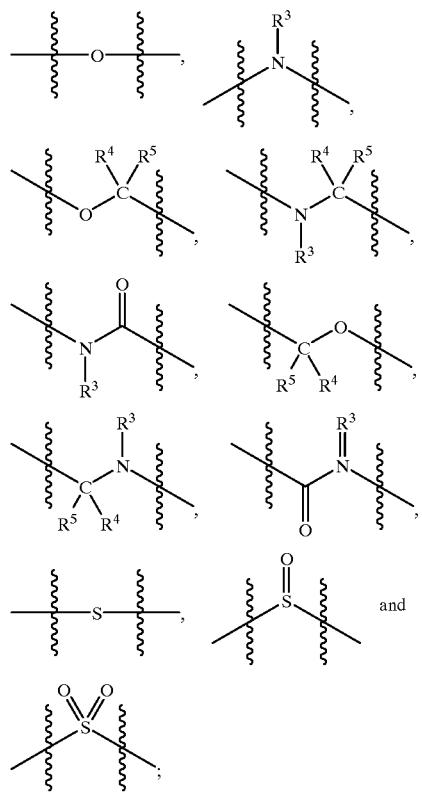

wherein $R^3$ is selected from the group consisting of hydrido, alkyl, carboalkoxy, and carboxyamido;

(c) wherein each of X and Y is independently selected from the group consisting of CH and N;
(d) wherein Z is selected from the group consisting of

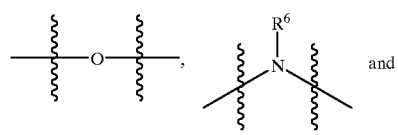

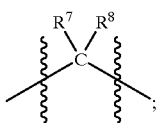

(e) wherein M is selected from the group consisting of hydrido, alkyl, aryl, carboxy and carboalkoxy;
(f) wherein D is selected from the group consisting of hydrido, aryl, heteroaryl, and alkyl; alternatively, M and D together are selected from the group consisting of

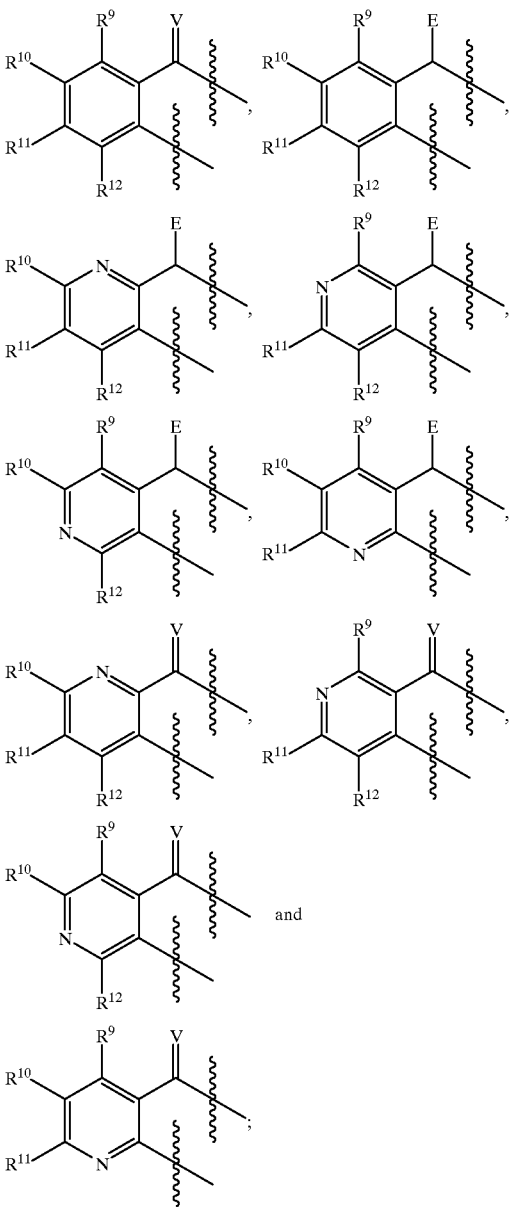

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected fom the group consisting of

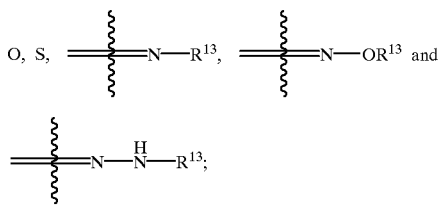

wherein B is selected from the group consisting of

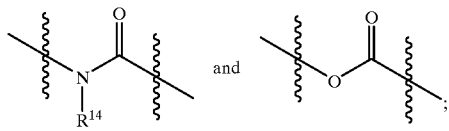

wherein each of $R^4$, $R^5$, $R^6$, $R^7$, $R^8$, $R^{13}$, and $R^{14}$ is independently selected from the group consisting of alkyl and hydrido; and pharmaceutically-acceptable salts thereof.

2. A preferred compound of the Formula:

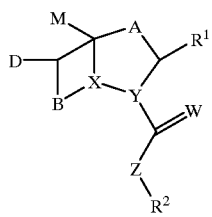

(a) wherein each of $R^1$ and $R^2$ is independently selected from the group consisting of aryl and heteroaryl;
(b) wherein A is selected from the group consisting of

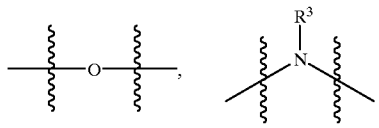

wherein $R^3$ is selected from the group consisting of hydrido, alkyl, carboalkoxy, and carboxyamido;
(c) wherein each of X and Y is independently selected from the group consisting of CH and N;
(d) wherein Z is selected from the group consisting of

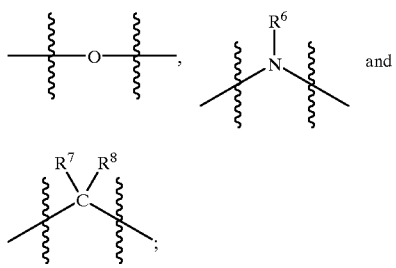

(e) wherein M is selected from the group consisting of hydrido, alkyl, aryl, carboxy and carboalkoxy;

(f) wherein D is selected from the group consisting of hydrido, aryl, heteroaryl, and alkyl; alternatively, M and D together are selected from the group consisting of

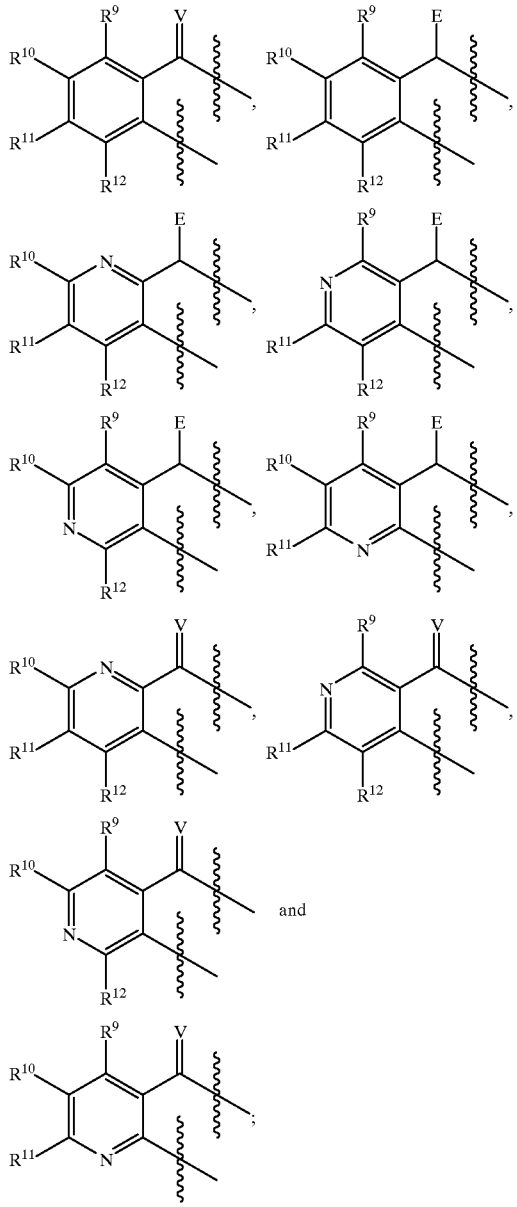

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected from the group consisting of

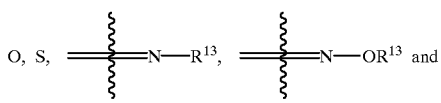

-continued

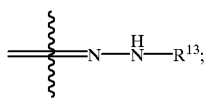

wherein B is selected from the group consisting of

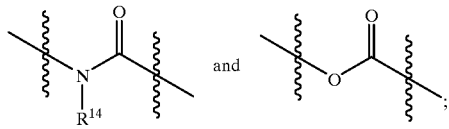

wherein each of $R^4$, $R^5$, $R^6$, $R^7$, $R^8$, $R^{13}$, and $R^{14}$ is independently selected from the group consisting of alkyl and hydrido;

and pharmaceutically-acceptable salts thereof.

3. A more preferred compound of the Formula:

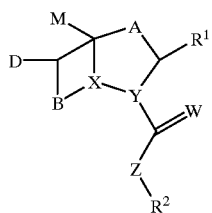

(a) wherein each of $R^1$ and $1^2$ is independently selected from the group consisting of aryl and heteroaryl;
(b) wherein A is selected from the group consisting of

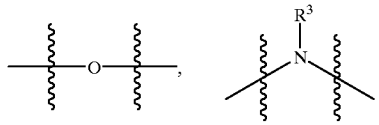

wherein $R^3$ is selected from the group consisting of hydrido, alkyl, carboalkoxy, and carboxyamido;

(c) wherein each of X and Y is CH;
(d) wherein Z is

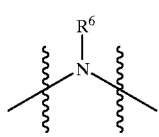

(e) wherein M is selected from the group consisting of hydrido, alkyl, aryl, carboxy and carboalkoxy;
(f) wherein M and D together are selected from the group consisting of

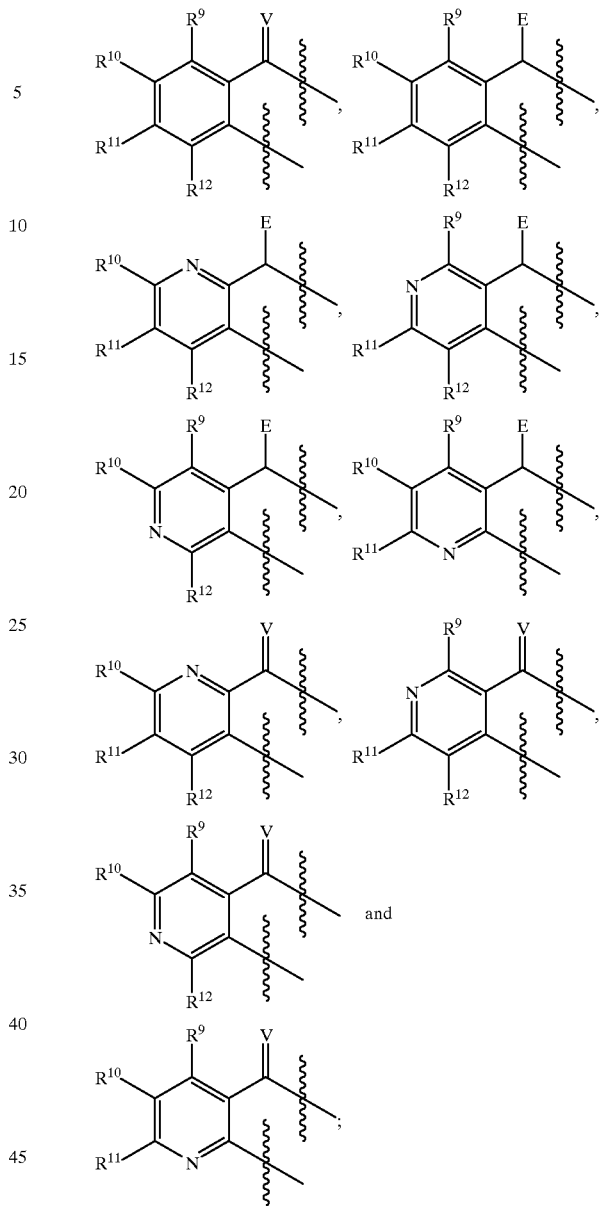

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected from the group consisting of O, S, (g) wherein B is

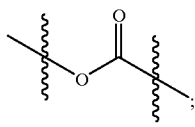

wherein each of $R^4$, $R^5$, $R^6$, and $R^{13}$ is independently selected from the group consisting of alkyl and hydrido;
and pharmaceutically-acceptable salts thereof.

4. A pharmaceutical composition comprising a therapeutically-effective amount of an active compound and a pharmaceutically-acceptable carrier, said active compound selected from a family of compounds of the Formula:

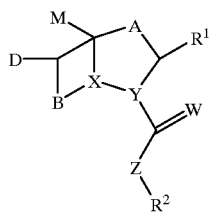

(a) wherein each of $R^1$ and $R^2$ is independently selected from the group consisting of aryl and heteroaryl;

(b) wherein A is selected from the group consisting of

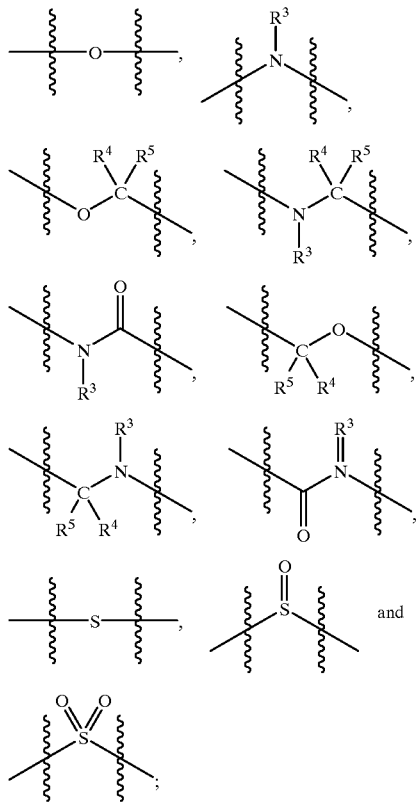

wherein $R^3$ is selected from the group consisting of hydrido, alky, carboalkoxy, and carboxyamido;

(c) wherein each of X and Y is independently selected from the group consisting of CH and N;

(d) wherein Z is selected from the group consisting of

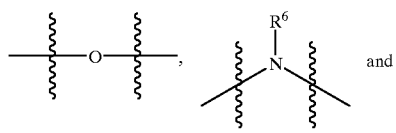

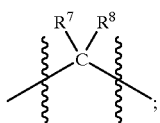

(e) wherein M is selected from the group consisting of hydrido, alkyl, aryl, carboxy and carboalkoxy;

(f) wherein D is selected from the group consisting of hydrido, aryl, heteroaryl, and alkyl; alternatively, M and D together are selected from the group consisting of

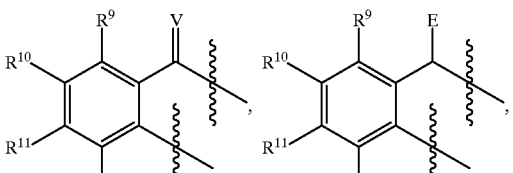

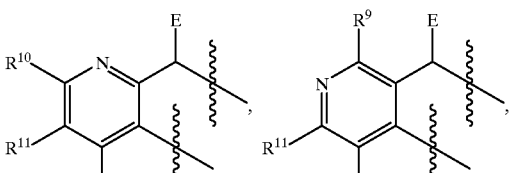

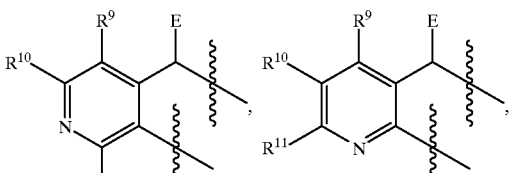

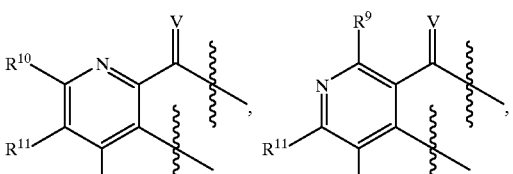

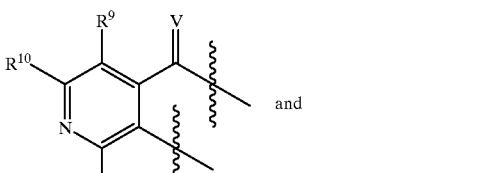

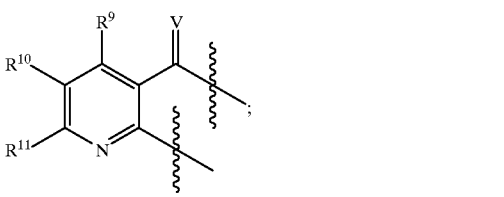

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected from the group consisting of

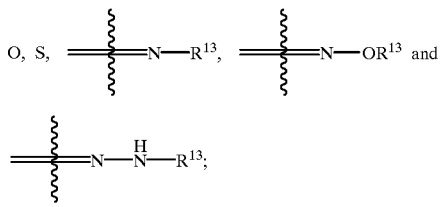

wherein B is selected from the group consisting of

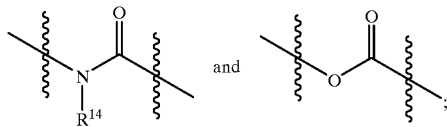

wherein each of $R^4$, $R^5$, $R^6$, $R^7$, $R^8$, $R^{13}$, and $R^{14}$ is independently selected from the group consisting of alkyl and hydrido; and pharmaceutically-acceptable salts thereof.

5. A pharmaceutical composition comprising a therapeutically-effective amount of an active compound and a pharmaceutically-acceptable carrier, said active compound selected from a family of preferred compounds of the Formula:

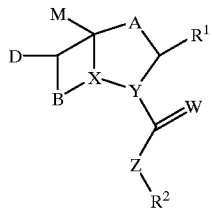

(a) wherein each of $R^1$ and $R^2$ is independently selected from the group consisting of aryl and heteroaryl;

(b) wherein A is selected from the group consisting of

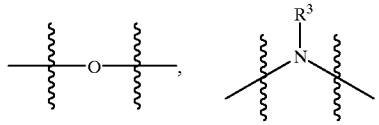

wherein $R^3$ is selected from the group consisting of hydrido, alkyl, carboalkoxy, and carboxyamido;

(c) wherein each of X and Y is independently selected from the group consisting of CH and N;

(d) wherein Z is selected from the group consisting of

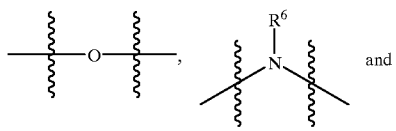

-continued

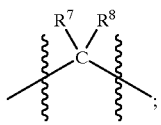

(e) wherein M is selected from the group consisting of hydrido, alkyl, aryl, carboxy and carboalkoxy;

(f) wherein D is selected from the group consisting of hydrido, aryl, heteroaryl, and alkyl; alternatively, M and D together are selected from the group consisting of

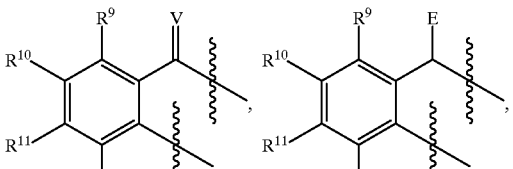

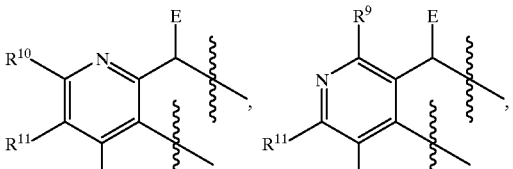

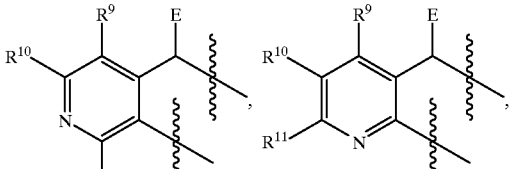

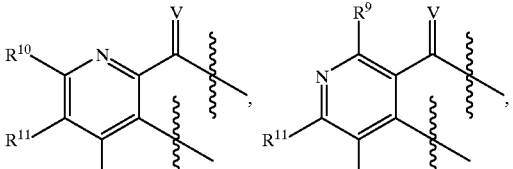

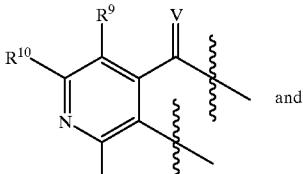

and

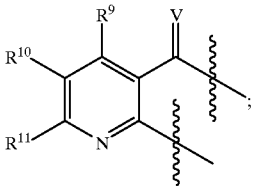

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected from the group consisting of

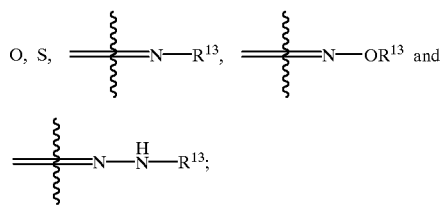

wherein B is selected from the group consisting of

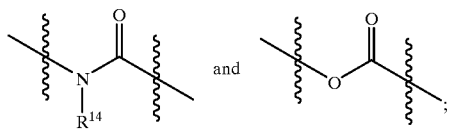

wherein each of $R^4$, $R^5$, $R^6$, $R^7$, $R^8$, $R^{13}$, and $R^{14}$ is independently selected from the group consisting of alkyl and hydrido;

and pharmaceutically-acceptable salts thereof.

6. A pharmaceutical composition comprising a therapeutically-effective amount of an active compound and a pharmaceutically-acceptable carrier, said active compound selected from a family of more preferred compounds of the Formula:

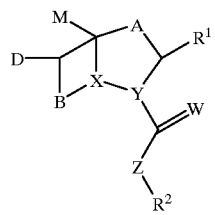

(a) wherein each of $R^1$ and $R^2$ is independently selected from the group consisting of aryl and heteroaryl;
(b) wherein A is selected from the group consisting of

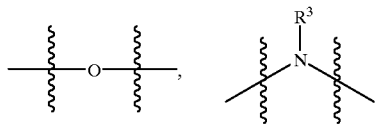

wherein $R^3$ is selected from the group consisting of hydrido, alkyl, carboalkoxy, and carboxyamido;
(c) wherein each of X and Y is CH;
(d) wherein Z is

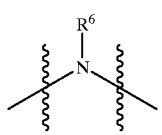

(e) wherein M is selected from the group consisting of hydrido, alkyl, aryl, carboxy and carboalkoxy;
(f) wherein M and D together are selected from the group consisting of

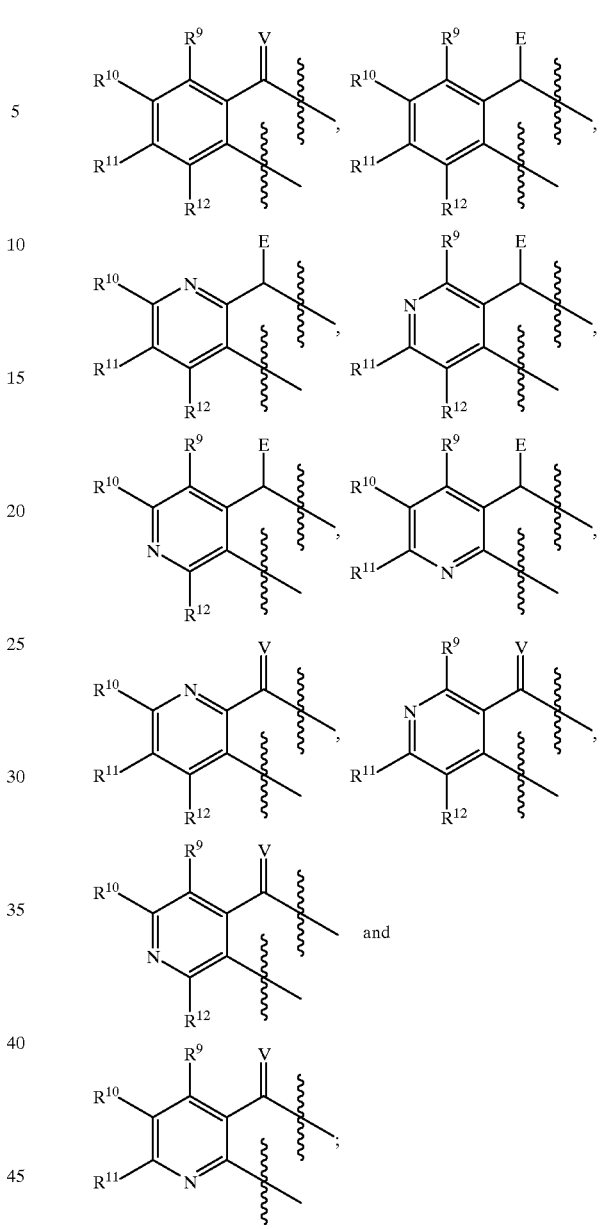

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected from the group consisting of O, S, (h) wherein B is

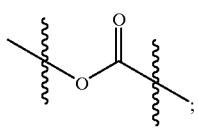

wherein each of $R^4$, $R^5$, $R^6$ and $R^{13}$ is independently selected from the group consisting of alkyl and hydrido;

and pharmaceutically-acceptable salts thereof.

7. A method of treating a subject afflicted by or susceptible to an infection, wherein said subject is selected from the group consisting of a mammal, a plant and a culture, said method comprising administering to the subject a therapeutically-effective amount of the compound of the Formula:

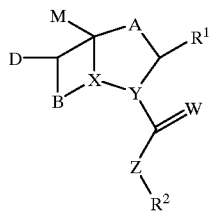

(a) wherein each of $R^1$ and $R^2$ is independently selected from the group consisting of aryl and heteroaryl;

(b) wherein A is selected from the group consisting of

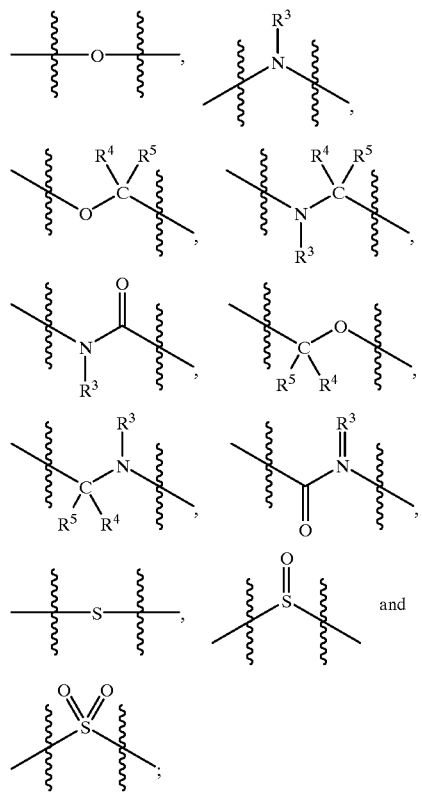

wherein $R^3$ is selected from the group consisting of hydrido, alkyl, carboalkoxy, and carboxyamido;

(c) wherein each of X and Y is independently selected from the group consisting of CH and N;

(d) wherein Z is selected from the group consisting of

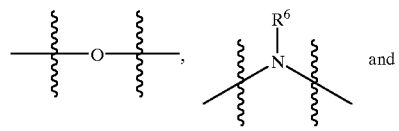

-continued

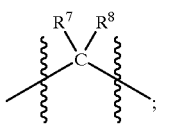

(e) wherein M is selected from the group consisting of hydrido, alkyl, aryl, carboxy and carboalkoxy;

(f) wherein D is selected from the group consisting of hydrido, aryl, heteroaryl, and alkyl; alternatively, M and D together are selected from the group consisting of

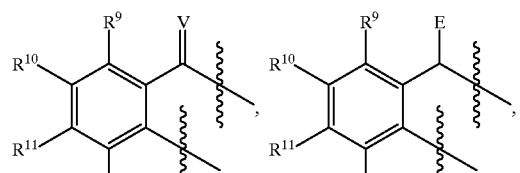

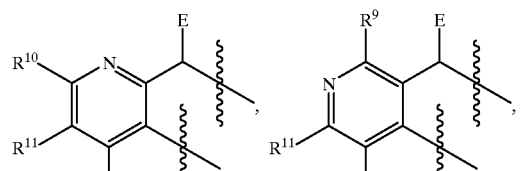

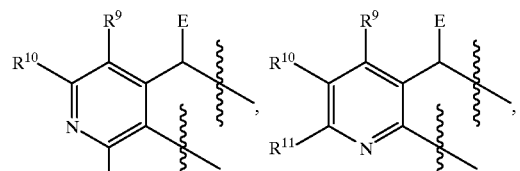

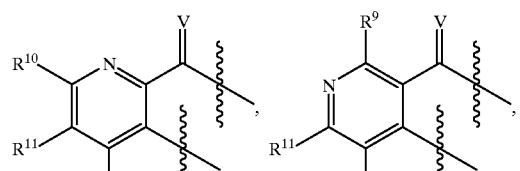

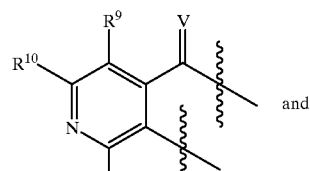

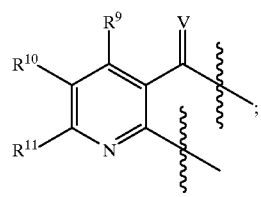

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected from the group consisting of

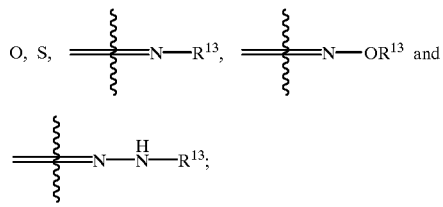

wherein B is selected from the group consisting of

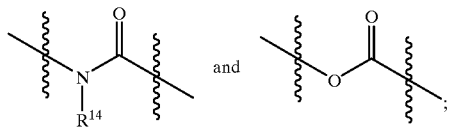

wherein each of $R^4$, $R^5$, $R^6$, $R^7$, $R^8$, $R^{13}$, and $R^{14}$ is independently selected from the group consisting of alkyl and hydrido; and pharmaceutically-acceptable salts thereof.

8. A method of treating a subject afflicted by or susceptible to an infection, wherein said subject is selected from the group consisting of a mammal, a plant and a culture, said method comprising administering to the subject a therapeutically-effective amount of the preferred compound of the Formula:

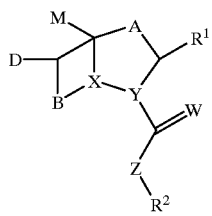

(a) wherein each of $R^1$ and $R^2$ is independently selected from the group consisting of aryl and heteroaryl;

(b) wherein A is selected from the group consisting of

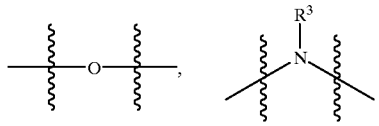

wherein $R^3$ is selected from the group consisting of hydrido, alkyl, carboalkoxy, and carboxyamido;

(c) wherein each of X and Y is independently selected from the group consisting of CH and N;

(d) wherein Z is selected from the group consisting of

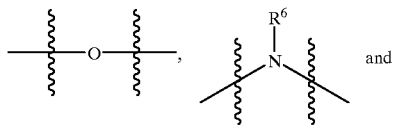

-continued

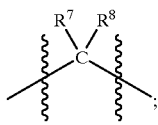

(e) wherein M is selected from the group consisting of hydrido, alkyl, aryl, carboxy and carboalkoxy;

(f) wherein D is selected from the group consisting of hydrido, aryl, heteroaryl, and alky; alternatively, M and D together are selected from the group consisting of

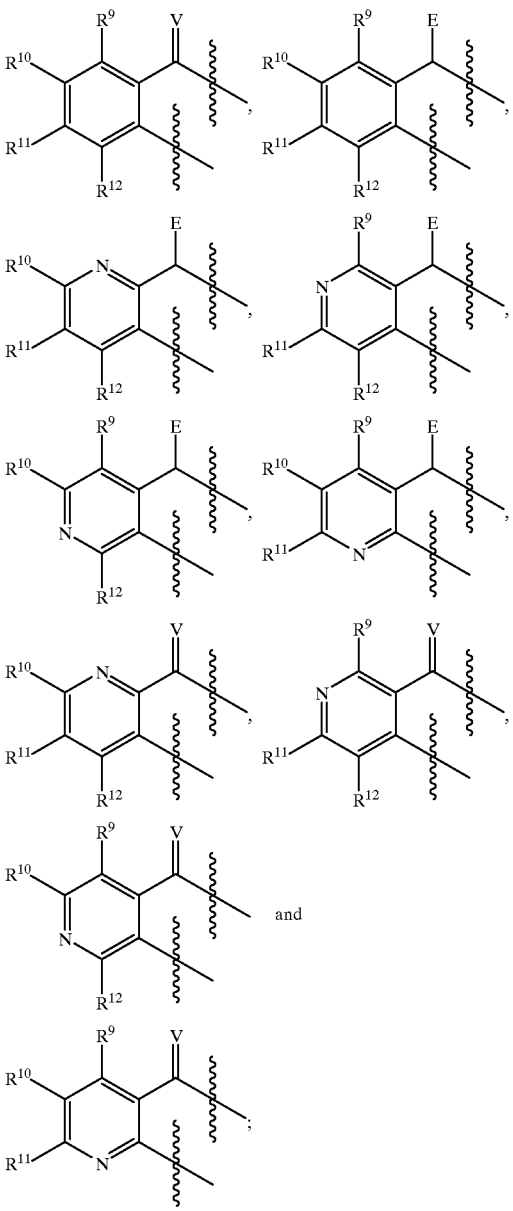

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected from the group consisting of

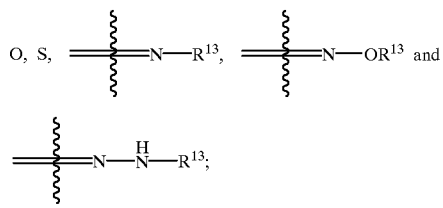

wherein B is selected from the group consisting of

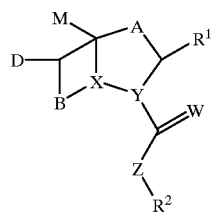

wherein each of $R^4$, $R^5$, $R^6$, $R^7$, $R^8$, $R^{13}$, and $R^{14}$ is independently selected from the group consisting of alkyl and hydrido; and pharmaceutically-acceptable salts thereof.

9. A method of treating a subject afflicted by or susceptible to an infection, wherein said subject is selected from the group consisting of a mammal, a plant and a culture, said method comprising administering to the subject a therapeutically-effective amount of the more preferred compound of the Formula:

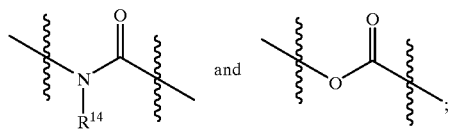

(a) wherein each of $R^1$ and $R^2$ is independently selected from the group consisting of aryl and heteroaryl;
(b) wherein A is selected from the group consisting of

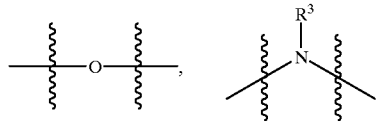

wherein $R^3$ is selected from the group consisting of hydrido, alkyl, carboalkoxy, and carboxyamido;
(c) wherein each of X and Y is CH;
(d) wherein Z is selected from the group consisting of

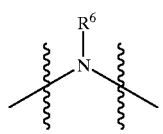

(e) wherein M is selected from the group consisting of hydrido, alkyl, aryl, carboxy and carboalkoxy;
(f) wherein M and D together are selected from the group consisting of

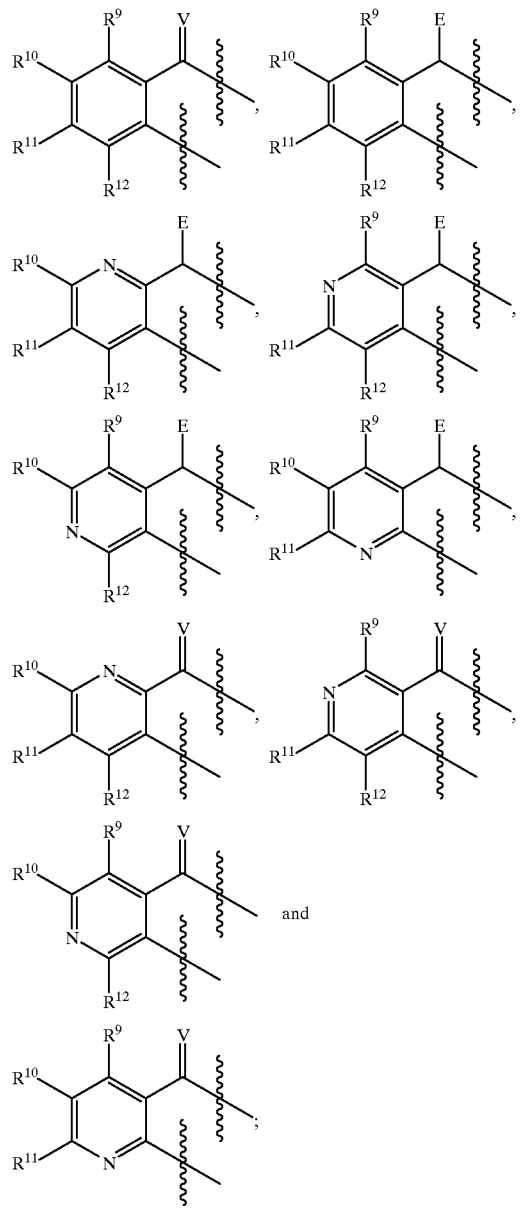

wherein each of $R^9$, $R^{10}$, $R^{11}$, and $R^{12}$ is independently selected from the group consisting of hydrido, halo, alkoxy and alkyl; wherein E is selected from the group consisting of hydrido, hydroxy, alkoxy, aryloxy, halo and amino; wherein V and W are independently selected from the group consisting of O, S, (i) wherein B is

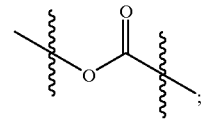

wherein each of $R^4$, $R^5$, $R^6$ and $R^{13}$ is independently selected from the group consisting of alkyl and hydrido; and pharmaceutically-acceptable salts thereof.

10. The method of claim 7 wherein the infection is a bacterial infection.

11. The method of claim 7 wherein the infection is a fungal infection.

12. The method of claim 7 wherein the subject is a mammal.

13. The method of claim 8 wherein the infection is a bacterial infection.

14. The method of claim 8 wherein the infection is a fungal infection.

15. The method of claim 8 wherein the subject is a mammal.

16. The method of claim 9 wherein the infection is a bacterial infection.

17. The method of claim 9 wherein the infection is a fungal infection.

18. The method of claim 9 wherein the subject is a mammal.

19. The method of claim 12 wherein the mammal is a human.

20. The method of claim 15 wherein the mammal is a human.

21. The method of claim 18 wherein the mammal is a human.

22. A method of inhibiting an aminoacyl-tRNA synthetase comprising contacting said aminoacyl-tRNA synthetase with a compound as claimed in claim 1.

23. A method of inhibiting an aminoacyl-tRNA synthetase comprising contacting said aminoacyl-tRNA synthetase with a compound as claimed in claim 2.

24. A method of inhibiting an aminoacyl-tRNA synthetase comprising contacting said aminoacyl-tRNA synthetase with a compound as claimed in claim 3.

25. A method of inhibiting the growth of microorganisms, comprising exposing said organisms to a compound claimed in claim 1.

26. A method of inhibiting the growth of microorganisms, comprising exposing said organisms to a compound claimed in claim 2.

27. A method of inhibiting the growth of microorganisms, comprising exposing said organisms to a compound claimed in claim 3.

* * * * *